(12) United States Patent
Dasgupta et al.

(10) Patent No.: US 7,306,720 B2
(45) Date of Patent: Dec. 11, 2007

(54) MEMBRANE BASED VOLATILE COMPONENT-REMOVAL DEVICES FOR LIQUID CHROMATOGRAPHY

(75) Inventors: Purnendu K. Dasgupta, Lubbock, TX (US); S. M. Rahmat Ullah, Lubbock, TX (US); Kannan Srinivasan, Tracy, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 10/924,236

(22) Filed: Aug. 23, 2004

(65) Prior Publication Data

US 2006/0037911 A1  Feb. 23, 2006

(51) Int. Cl.
*B01D 15/08* (2006.01)

(52) U.S. Cl. ............... 210/198.2; 210/180; 210/188; 210/656; 422/70

(58) Field of Classification Search ............ 210/635, 210/656, 659, 188, 198.2, 180; 422/70
See application file for complete search history.

(56) References Cited

U.S. PATENT DOCUMENTS

| | | |
|---|---|---|
| 3,751,879 A | 8/1973 | Allington et al. |
| 3,897,213 A | 7/1975 | Stevens et al. |
| 3,920,397 A | 11/1975 | Small et al. |
| 3,925,019 A | 12/1975 | Small et al. |
| 3,926,559 A | 12/1975 | Stevens |
| 4,474,664 A | 10/1984 | Stevens et al. |
| 4,533,518 A | 8/1985 | Hanaoka et al. |
| 4,977,008 A | 12/1990 | Squire |
| 4,999,098 A | 3/1991 | Pohl et al. |
| 5,248,426 A | 9/1993 | Stillian et al. |
| 5,439,736 A | 8/1995 | Nomura |
| 5,597,481 A | 1/1997 | Stillian et al. |
| 5,773,615 A | 6/1998 | Small et al. |
| 6,444,475 B1 | 9/2002 | Anderson, Jr. et al. |
| 6,495,371 B2 | 12/2002 | Small et al. |

FOREIGN PATENT DOCUMENTS

| | | |
|---|---|---|
| EP | 1 074 837 A1 | 2/2001 |
| WO | WO 98/17362 A1 | 4/1998 |
| WO | WO 2005/047885 A2 | 5/2005 |
| WO | WO 2005/047885 A3 | 5/2005 |

OTHER PUBLICATIONS

Boring, C., et al., "Field measurement of acid gases and soluble anions in atmospheric particulate matter using a parallel plate wet denuder and an alternating filter-based automated analysis system" *Anal. Chem.* 74(6):1256-1268 (Mar. 2002) (pub'd online Feb. 9, 2002).

(Continued)

*Primary Examiner*—Ernest G. Therkorn
(74) *Attorney, Agent, or Firm*—Morgan, Lewis & Bockius LLP; David J. Brezner

(57) ABSTRACT

In a liquid chromatographic system, removing at least part of a volatile component from the liquid sample stream after separation by flowing it through a volatile component-removal device including a porous wall having a surface coating of a permeable polymer less than 10 µm thick. A liquid chromatographic system suitable for performing the method. Also, a liquid chromatographic system in which volatile component is removed prior to separation across the same type of membrane or across a membrane made of a copolymer of perfluoro-2,2-dimethyl-1,3-dioxole.

4 Claims, 17 Drawing Sheets

OTHER PUBLICATIONS

Majors, R., "New chromatography columns and accessories at the 2004 Pittcon Conference, Part II," *LCGC* 22(4) (Apr. 2004).

Novič, M., et al., "Carbonate interferences by ion chromatographic determination of anions in mineral waters," *J. Chromatogr. A* 764(2):249-256 (Mar. 1997).

Rahmat Ullah, S.M., et al., "Asymmetrical membrane fiber-based carbon dioxide removal devices for ion chromatography," *Anal. Chem.* 76(23):7084-7093 (Dec. 2004) (first pub'd online Oct. 21, 2004).

Reim, R., "Postcolumn deoxygenator for liquid chromatography with reductive electrochemical detection," *Anal. Chem.* 55(7):1188-1191 (Jun. 1983).

Shintani, H., et al., "Gradient anion chromatography with hydroxide and carbonate eluents using simultaneous conductivity and pH detection," *Anal. Chem.* 59(6):802-808 (Mar. 1987).

Siemer, D., et al., "Silicone rubber tubing for elimination of background conductivity in anion chromatography," *Anal. Chem.* 56(6):1033-1034 (May 1984).

Sunden, T., et al., "Carbon dioxide permeable tubings for post-suppression in ion chromatography," *Anal. Chem.* 56(7):1085-1089 (Jun. 1984).

MEMBRANE BASED VOLATILE COMPONENT-REMOVAL DEVICES FOR LIQUID CHROMATOGRAPHY

BACKGROUND OF THE INVENTION

The present invention relates to the removal of gases such as $CO_2$ from analyte streams in liquid chromatography.

The process of suppression as currently practiced minimizes the conductivity of the eluent or mobile phase while maximizing the conductivity of most analytes. This technique is described in several patents (U.S. Pat. Nos. 3,897,213; 3,920,397; 3,925,019; 3,926,559, 4,474,664, 4,999,098).

In HPLC applications with electrochemical detection the presence of oxygen leads to higher background current and noise. Reim in *Anal. Chem*, 55, 1983, 1188-1191, showed that the oxygen background can be minimized with the use of gas permeable tubing. The tubings tested for oxygen gas permeability were silicone rubber, Teflon®, 4-methyl-1-pentene, Tygon® and Nafion®. Silicone rubber tubing was chosen because of its higher permeability. Evacuating the outside of the tubing was more effective in oxygen removal versus purging with an inert gas or flushing the outside with an alkaline sulfite sweep solution. The other tubings used in the above investigation had lower permeability to $CO_2$ along with the limitation that the $CO_2$ had to traverse through the tubing wall material. The silicone rubber tubings used in the above work however were fragile. Therefore, there is a need for a pressure stable gas permeable membrane that would be useful for removing $O_2$ from the eluent.

In suppressed IC with carbonate eluents, it was recognized early by some workers that removing the $CO_2$ from a carbonic acid suppressed eluent would allow the implementation of gradients using carbonate and/or bicarbonate eluents. The removal of $CO_2$ led to lower background along with other benefits such as reduction of the water dip or void peak, better integration of the early eluting peaks from the void, lower noise because the background is lower, and higher sensitivity depending on the background. However, the tubings used in the above work were fragile and in some cases had pinholes allowing liquid transport across the tubing walls. Therefore there is a need for pressure stable gas permeable membranes that would be useful for removing $CO_2$ from the suppressed eluent without allowing bulk liquid flow.

During suppressed IC analysis, the peak constituting dissolved $CO_2$ in the sample is detected as suppressed carbonic acid. In some samples this carbonate peak appears as a relatively broad tailing peak and depending on the concentration can interfere with the identification and quantitation of anions that elute in the general vicinity during elution with hydroxide or borate eluents. The problem is particularly acute when a large sample volume is injected. Sample degassing by sonication or by bubbling $N_2$ or helium gas are commonly used to minimize the intrusion of $CO_2$ into the sample. The above approaches work best for acidic samples (pH<6.3, pKa of H2CO3) as dissolved $CO_2$ is largely present in the unionized form and would tend to outgas easily. In alkaline (basic) samples, however the dissolved $CO_2$ is largely present in the ionized form (as bicarbonate and carbonate) anion and cannot be easily removed by degassing approaches. There is a need therefore for a simple online means of removing $CO_2$ from samples for ion chromatography. The role of the prior art gas permeable modules in IC was to remove carbon dioxide from carbonate eluents after suppression. With carbonate eluents, the presence of relatively higher levels of dissolved carbon dioxide in the sample is usually obscured by the high $CO_2$ background from the suppressed eluent (carbonic acid). However in some samples the presence of high concentrations of dissolved $CO_2$/carbonate may still cause problems with the analysis.

U.S. Pat. No. 5,439,736 describes fully alkylated polysiloxane polymer deposited from the gas phase on microporous polymeric hollow fibers. The resulting coating is a thin film crosslinked on the outside of the fibers. Plasma polymerization conditions are stated to lead to uniform, pinhole free, highly adherent and ultra thin coatings. In U.S. Pat. No. 5,439,736 the above cited tubings were stated to be useful for gas phase separations.

Sunden et. al., *Anal. Chem.* 1984, 56, 1085-1089, described the use of porous PTFE tubings (Goretex®) for the purpose of lowering the background conductivity using hydrogen carbonate/carbonate eluents. By inserting a twisted wire into the gas permeable tubing the authors stated they were able to remove about 90% of the carbon dioxide.

Siemer and Johnson, *Anal. Chem*. 1984, 56, 1033-1034, in 1984 used silicone tubing for carbon dioxide removal from carbonate/bicarbonate eluents. A 0.1 M KOH solution was warmed and used in the exterior of the silicone rubber tubing. almost complete removal of $CO_2$ was stated to be accomplished by warming the or solution to about 79° C.

In general, the above tubings tended to be fragile and did not offer the pressure stability offered by tubings of the present invention. In some of the above tubings, the diffusion length through the wall of the tubing was significantly large.

Shintani and Dasgupta, *Anal. Chem. (*1987), 802-808, disclosed a bundle of porous polypropylene tubing coated with silicone as post suppressor devices for lowering the background conductivity with carbonate/bicarbonate eluents. The authors concluded that a baseline correction by subtracting the background (run without injection from a standard run) was better than the use of the above gas permeable post suppressor device. The coating method suggested a thick coating density on the outside of the polypropylene fiber. For example, the above publication recommends that the tubing be coated up to 10 times in order to get a pin hole free tubing.

U.S. Pat. No. 6,444,475 described the use of TEFLON AF gas permeable tubing for the function of removing $CO_2$ from the suppressed carbonate and/or bicarbonate eluents. Although the tubing is described to be pressure resilient, it is extremely expensive.

Therefore, there is a need for a pressure resilient, efficient low cost alternative to the foregoing materials.

When using a preconcentration technique in anion analysis the presence of excessive amounts of carbon dioxide/carbonate in the sample stream will affect the performance of the concentrator column, as the concentrator column will concentrate the carbonate ion along with other sample anions of interest. In addition to reducing the effective capacity of the concentrator the presence of carbon dioxide/carbonate in the sample can also impact the capture efficiency of the concentrator column as the carbonate ions tend to elute the other sample ions of interest. The peak shapes can also suffer because the sample plug is diffused in the concentrator due to partial elution and the sample is injected as a broad plug into the separator. Therefore there is a need for removing carbon dioxide/carbonate in sample streams particularly while using a preconcentrator column.

Similarly in cation analysis, presence of high levels of ammonia during the preconcentration step has a deleterious effect as discussed above. Therefore there is a need for removing the interference of ammonia in sample streams.

SUMMARY OF THE INVENTION

In one embodiment, the invention comprises a liquid chromatographic method including removal of a volatile component from an aqueous liquid sample stream, the method comprising (a) chromatographically separating analytes in a liquid sample stream including a volatile component, and (b) removing at least part of a volatile component from the liquid sample stream from step (a) by flowing it through a volatile component-removal device comprising at least one porous wall having a surface coated with a polymer permeable to the volatile component, the coating thickness being less than 10 µm.

In another embodiment, the invention comprises a liquid chromatographic system comprising (a) a liquid chromatographic column having an inlet and an outlet and (b) a volatile component-removal device comprising a membrane comprising at least one porous wall having a surface coated with a coating of polymer, the coating having a thickness less than 10 µm, the device defining a liquid sample stream flow channel having an inlet and an outlet, the liquid sample stream flow channel inlet being in fluid communication with the chromatographic column outlet.

In another embodiment, the invention comprises a liquid chromatographic method including removal of a volatile component from an aqueous liquid sample stream, the method comprising (a) removing at least part of a volatile component from a liquid sample stream containing it by flowing it along one side of a membrane in a removal device, the membrane comprising at least one porous wall having a surface coated with a coating of a gas-permeable polymer, the coating thickness being less than 10 µm (b) after step (a), chromatographically separating analytes in the liquid sample stream.

In a further embodiment, the invention comprises a liquid chromatographic system comprising (a) a volatile component removal device comprising at least one membrane defining a liquid stream sample flow channel, the device having an inlet and an outlet, the membrane comprising at least one porous wall having a surface coated with a coating of polymer, the coating thickness being less than 10 µm (b) a liquid chromatographic column, the volatile component-removal device outlet being in fluid communication with the chromatographic column.

In another embodiment, the volatile component permeable membrane in the system of the previous paragraph is an amorphous copolymer of perfluoro-2,2-dimethyl-1,3-dioxole.

Figure 1:
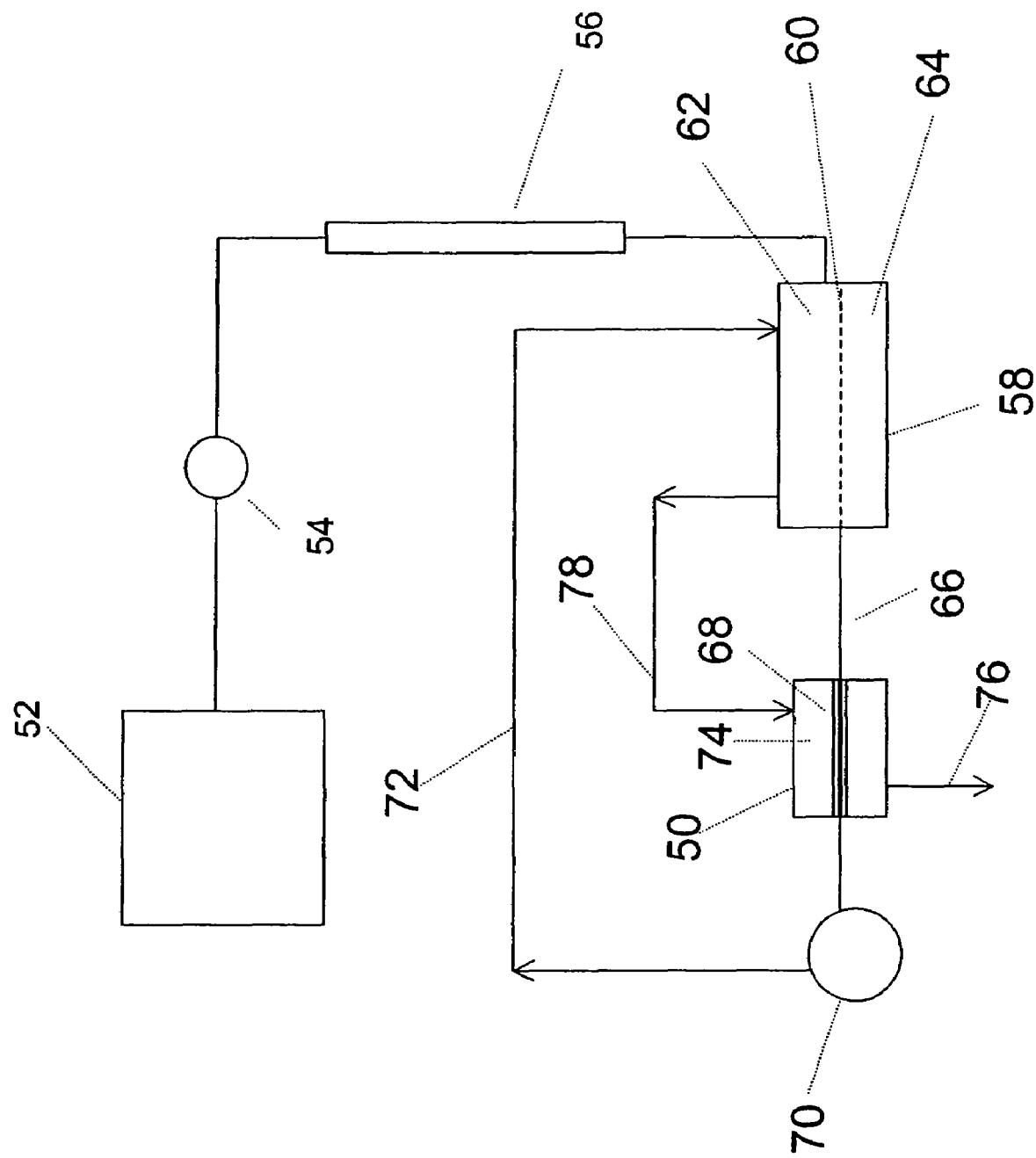
FIGS. 1, 14 and 15 are schematic representations of apparatus according to the invention.

The figure shows comparison chromatograms of a seven anion standard sample obtained without and with a GRD installed.

DETAILED DESCRIPTION OF THE INVENTION

In one embodiment, the present invention relates to a gas or other volatile component-removal device (GRD) comprising a thin coating on the surface of a porous polymer substrate of a different material. Such a combination according to the present invention allows for gas removal from liquid streams for chromatographic applications. Such coated membranes are termed "asymmetric membranes" meaning they have coatings on a host porous substrate of a different material. The coating can be on one side or on both sides of the porous host surface.

In general, preferable characteristics of the coating are as follows. The coating should be permeable to the component of interest. The coating should be relatively thin to minimize the diffusion distance of the removed component and thereby facilitating fast removal of the said component from the flowing liquid stream. The coating should be uniform and substantially completely cover the substrate thereby substantially blocking bulk liquid flow particularly when used with liquid streams on both sides of the membrane.

In one embodiment, the above coated polymeric substrates are useful for removing $CO_2$ and/or other volatile components from suppressed liquid eluent streams prior to detection in ion chromatography. Preferably, the asymmetric membranes have a coating thickness of less than 10 microns, and more preferably less than 5, 4, 3, 2 or 1 microns, more preferably in the range of 0.02 to 3 micron and most preferably between 1 and 3 microns. The purpose of the thin film coating is to aid removal of volatile species such as $CO_2$ from a liquid stream. The thin dimension of the exterior film allows for efficient removal of gas from the liquid streams in chromatographic applications.

The porous host substrate or wall of the present invention can be any material of sufficient porosity. Suitable substrates include porous polymers with pore sizes of about 0.01 micron to 100 microns. Preferably, the pore sizes are in the 0.02 to 1 micron range, more preferable in the 0.02 to 0.2 micron range. The thickness of the host substrate suitably is from about 1 to 1000 micron, more preferably between 10 and 100 micron thickness.

A preferred substrate material is a porous polypropylene fiber. However, other organic polymeric materials can be used for the tubing such as polyethylene or polystyrene as long as it has comparable porosity. The materials disclosed in U.S. Pat. No. 5,439,736 may be used including polymers from ethylenically unsaturated monomers such as polyolefins (e.g., polyethylene or polypropylene), substituted polyolefins, polysulfones, polystyrenes or condensation polymers (e.g., aromatics). Porous polypropylene hollow fibers are preferred such as are available from Hoechst Cealinese Corp., maker of Celgard X 20-240, and X 220-400 hollow fibers and Mitsubishi Rayon Company, maker of KPF 190M, 270B, 360A, 250M and 190G hollow fibers. Such fibers have pores which are generally elliptical in shape. The pores typically are about 6,000 Å long and the width varies from about 10 Å to about 650 Å or more. Mitsubishi KPF 190M membrane is particularly effective as a host membrane.

Other suitable host materials are porous non-polymeric supports such as silver membranes, ceramic membranes and the like.

The coatings can be made from polymers or monomers resulting in polymeric layers leading to coatings such as polymethyl siloxanes, alkylated siloxanes, for example, hexamethyl disiloxanes, polyalkyne based polymers and the like. Preferred coatings would have good permeability for the volatile ionogenic components of interest such as $CO_2$, $H_2S$, $SO_2$, $NH_3$, HCN, HCl etc or volatile nonionic components such as acetonitrile, ethanol, methanol, formaldehyde, etc. The term "volatile component" encompasses a compound carried by the liquid sample which is a gas at room temperature, such as $CO_2$, or one that is a liquid at room temperature but which tends to vaporize at a temperature of about 60° C. or less, e.g., ethanol.

A suitable coating includes a variety of siloxanes such as alkylated disiloxane and the specific siloxane disclosed in U.S. Pat. No. 5,439,736 as well as polybutadiene or silicone polycarbonate copolymer. Specific coatings may be made from polymers or monomers polymerized on the substrate of materials such as polymethyl siloxanes, alkylated siloxanes, e.g., hexa methyl disiloxanes, polyalkyne based polymers and the like. Preferred coatings would have high permeability for the species of interest. For example, the permeability for $CO_2$ for a preferred silicon rubber polymer is 4553 barrers (1 barrer=$10^{-10}$ cc-cm/(cm$^2$.s.cm.Hg)). The permeability of poly(trimethylsilyl-1-propyne) is 33,100 barrers. The gas phase plasma polymerization technique disclosed in that patent is incorporated herein by reference.

As used herein "permeability" for the volatile component of interest to be removed from the liquid stream in contact with the membrane can be assessed by the fractional removal achieved when a liquid stream containing the said component passes through the membrane based removal device. Such fractional removal is at least 50%, more preferably at least 60%, 70%, 80%, 90% or more. In a preferred embodiment, the removal of a volatile component, e.g., $CO_2$, is greater than 90%, more preferably at least 92, 94, 96, 98%, 99% or more. Percent $CO_2$ removal or reduction can be calculated from the residual background in the case of carbonate or bicarbonate eluent or the residual peak height of the $CO_2$ peak originating from dissolved $CO_2$ in the sample in the case of a hydroxide or borate eluent.

Alternatively, the permeability of the membrane may be determined by the permeability of the gas of interest to be removed in barrers as measured by the method of the '736 patent, preferably at least 100 barrers, more preferably at least 1,000 barrers, 30,000 barrers, 40,000 barrers or more.

In accordance with one embodiment, a method and apparatus are illustrated for the removal of a volatile component, e.g., $CO_2$, from a liquid sample stream from a chromatography column by flowing the stream through a GRD, including a permeable wall that is permeable to and preferably selectively permeable to the volatile component. In a preferred embodiment for removal of $CO_2$, the wall comprises a porous polymer substrate (e.g., porous polypropylene) having a surface coated with polysiloxane of a defined thickness. After passing through the GRD, the analytes in the liquid sample stream are detected.

The invention will first be described with respect to the structure of a GRD wherein the volatile component is $CO_2$ and the wall is in the form of porous tubing(s) or fiber(s). In general terms, this GRD includes a $CO_2$ permeable wall with a porous polymer substrate coated with a polysiloxane layer having a predetermined thickness. The polysiloxane coating may be made by the gas plasma polymerization technique described in U.S. Pat. No. 5,439,736 or by a modified version of the method described by Shintani, et al. paper in *Anal. Chem.* (1987), 59,802-808. The membrane of the present invention is substantially thinner than one inherently formed by the method of the Shintani, et al. publication. As set forth above, the membrane in Shintani was stated to be recoated repeatedly up to 10 times. This recommended coating procedure results in a relatively thick polysiloxane or silicon coating, e.g., greater than about 90 microns in thickness.

Commercial tubing supplied by NeoMecs under the name GasTran™ Hollow Fiber Membrane has a thinner polysiloxane coating (e.g., disiloxane coated on a polypropylene microporous hollow fiber). However, the U.S. Pat. No. 5,439,736 which describes a method of making tubing from this membrane only discloses use in gas separations.

In the simplest form of GRD, the coated gas permeable membrane tubing is installed inline with the liquid eluent stream. In one preferred embodiment, the GRD is installed after a suppressor device and before a detector in a chromatography system. The outside perimeter of the tubing may be exposed to the ambient environment or may be encased in an enclosure that would allow the exterior of the gas permeable membrane to be in contact with a fluid or would allow the use of vacuum.

In a preferred form of GRD, a gas-receiving liquid solution flows on the exterior of a liquid sample stream which flows in the lumen of the asymmetric tubing. In other applications, the outside perimeter of the tubing may be exposed to the ambient environment instead of being enclosed is a casing. The casing permits the flow of a gas or liquid in the exterior chamber or the use of a vacuum applied there to facilitate removal of the $CO_2$ or other gases. Alternatively, the liquid sample stream can flow on the outside of the tubing with a gas-receiving fluid flowing on the interior of the tubing. A basic aqueous solution may flow countercurrent to the $CO_2$-containing liquid on the opposite side of the asymmetric membrane in the GRD. Also, a vacuum can be pulled in the enclosure of the GRD without plugging the other end to allow air flow around the tubing. Further, a stationary fluid can be used in the cavity. The function of the fluid flow on the opposite side of the asymmetric wall from the liquid sample is to facilitate the removal of volatile components such as $CO_2$ or ammonia or methanol. Preferred fluids used for removal of the component of interest can be an aqueous solution, e.g., water, or a gas such as inert gas or air. Alternatively, the asymmetric wall may be a flat or other shaped membrane in a housing separating an exterior environment from the liquid sample solution containing the gas to be removed.

When the asymmetric wall of the present invention is in the form of tubing, the term "tubing" means a single length of tubing or multiple tubes in a bundle (e.g., the GRD of Shintani et al. with a fiber bundle of 10 fibers, each 30 cm long). However, as illustrated in the examples, in a preferred form of the invention, the tubing comprises a single length of fiber or tubing in one or more segments through which the entire liquid sample stream flows. A suitable length for a typical chromatography system operated at flow rates of 0.1-2 ml/min is from about 5 to 200 cm, more preferably from 50 to 150 cm. For capillary scale chromatography systems where the flow rate is much lower the length required will also be lower. Thus, the asymmetric membrane wall of the present invention can be in tubular or fiber form, single tubing or multiple tubing bundles. Also, it can be in the form of a flat membrane. Also, it can be flat or another shape bounding one side of a liquid sample stream flow channel.

The GRD of the present invention is particularly useful for suppressed chromatography in which the liquid sample stream containing the separated analytes from the chromatography column is passed through a suppressor in which the conductivity of the eluent stream is suppressed. For anion analysis, the analytes are converted into acid form. Also, an alkali metal carbonate/carbonate eluent is converted to carbonic acid form leading to a significant increase in $CO_2$ content in the sample stream leaving the suppressor. However, the GRD also could be used without such eluent to remove the $CO_2$ or other gases.

FIG. 1 illustrates one suppressed chromatography system using a GRD is illustrated. This system is applicable to the use of any $CO_2$ permeable tubing in the GRD, not just specific thin coated tubing described above.

Referring specifically to FIG. 1, the GRD 50 may be of the type illustrated in the examples including a single piece of porous asymmetric tubing highly permeable to a gas such as $CO_2$ with an external flow channel around the tubing. The eluent is pumped into the column by pump 52 and the liquid sample is injected at injection valve 54. The eluent along with the liquid sample flows through the chromatographic column 56 and from there to the inlet of a suppressor of the type of the flat membrane type and recycled from the detector to the regenerant flow channel of the suppressor such as described in U.S. Pat. No. 5,248,426. Such a suppressor includes one or more permselective membrane 60 separating a sample stream flow channel 62 from a regenerant stream flow channel 64. The sample stream flow channel flows in line 66 to the interior of volatile component permeable tubing 68 and from there to a detector cell such as conductivity detector cell 70. As illustrated in the '426 patent, after detection, the detected sample stream is recycled in line 72 to regenerant flow channel 64 (details not shown). The outlet of the regenerant flow channel 64 which would otherwise be passed to waste flows in line 78 to the exterior flow channel 74 surrounding tubing 68. As described herein, during anion analysis an aqueous liquid solution, preferably at an alkaline pH, flows through continuously through the exterior of tubing 68 to carry away the $CO_2$. The aqueous solution which flows through the exterior of the tubing can then be passed to waste as illustrated at 76. In the above embodiment any prior art suppressor could be used provided the suppressor waste is a base.

In one embodiment, for cation analysis, an aqueous liquid solution, preferably at acidic pH, flows through continuously through the exterior of tubing 68 to carry away the removed volatile component such as ammonia. The aqueous solution which flows through the exterior of the tubing can then be passed to waste as illustrated at 76. In the above embodiment any prior art suppressor could be used provided the suppressor waste is an acid.

In one embodiment, line 76 from the suppressor may be routed to waste. Under these conditions a liquid feed from an external reservoir (not shown) is routed through the exterior flow channel 74 and then routed to waste via tube 76.

As illustrated in FIG. 1, the GRD 50 comprises a tubing permeable to the volatile component to be removed, installed in an enclosure that accommodates fittings (not shown) allows easy plumbing of the unit to the IC system, a post suppressor embodiment of the present invention. The suppressor eluent out stream is plumbed into the inlet port of the device. The outlet port of the device is plumbed to the conductivity cell inlet.

The enclosure of GRD 50 in FIG. 1 has two fittings (not shown) for allowing fluidic connections. A vacuum may be pulled from one end while plugging the other end of the enclosure or a vacuum may be pulled without plugging the other end of the enclosure thereby allowing air flow around the tubing of the present invention. In the illustrated embodiment of the present invention the fluidic flow would be in a counter current direction to the sample stream. However, the device will work with concurrent fluid flow. In another embodiment the fluid would be stationary in the cavity. The function of the fluidic flow is to aid removal of the species. Preferred fluids would be air, inert gas or an aqueous medium preferably reactive to the removed gaseous species. A vacuum may be applied as an alternative to a fluid stream. As set forth above, basic flowing liquid stream exterior to tubing 60 would be preferred when the species to be removed is carbon dioxide since the base would react and convert the carbon dioxide to carbonate ion. A preferred basic stream would be in the form of the basic suppressor waste in anion analysis that could be diverted into the encasing and then subsequently diverted to waste as shown in FIG. 1. Thus, under the above plumbing configuration a self sustained source of base is available from the suppressor waste stream.

Similarly for removing gaseous species such as ammonia during cation analysis a preferred acidic stream would be in the form of the suppressor acid waste that could be diverted into the encasing and subsequently diverted to waste. This aspect of the present invention is unique and will work with all prior art gas permeable tubings (including Teflon AF). The fluidic streams may be heated as required.

In the embodiment of FIG. 1, the eluent stream may also be pumped on the outside of the tubing while the interior of the tubing is swept with a waste base stream. The coated membranes of the present invention can be in tubular fiber form as a single fiber or tubing or multiple fiber bundle or in flat membrane configuration. Such tubular fibers can be packed with functionalized materials or neutral materials, for example, a nylon filament can be inserted into the inside of the tubing. The function of the packing would be to promote mixing or diffusion to the walls of the tubing. The exterior of the membrane can also be packed with functionalized or neutral materials. In the flat membrane configuration the device could have gasketed screen materials to define the flow pathway similar to flat membrane suppressor devices of the prior art. Preferred means of dispensing base stream would be by gravity feed or by pressure feed from a reservoir containing base.

The interior of the tubing may be packed with functional or neutral materials such as a nylon filament inside the tubing to promote mixing or diffusion of the walls of the gas permeable tubing. Also, the exterior of the membrane can be packed with functionalized or neutral materials such as of the type described in the '426 patent.

The following equation describes the chemical equilibrium existing in the suppressed eluent particularly for a carbonate and/or bicarbonate eluent system.

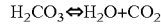

$$H_2CO_3 \Leftrightarrow H_2O + CO_2$$

By removing the $CO_2$, the equilibrium is driven to the right there by reducing the $H_2CO_3$ (suppressed carbonic acid) concentration and hence lowering the background conductivity. The $CO_2$ molecules selectively diffuse through the selective barrier while the external fluid aids in the removal of the permeated $CO_2$ to waste.

$H_2CO_3$ is a weak acid with a $K_1$ of $7.47 \times 10^{-7}$ at 25° C. For solutions of $H_2CO_3$, the second dissociation step plays no significant role. The ionic composition of an $H_2CO_3$ solution is readily solved by solving the relevant charge and mass balance equations. The conductance of the solution can then be calculated from the known ionic equivalent conductance values. The relationship between the conductance and concentration of $H_2CO_3$ is highly nonlinear; removal of some of the $H_2CO_3$ results in better ionization of the remaining concentration, so that reduction in the $H_2CO_3$ is not proportionally reflected in the conductance. When $CO_2$ is removed from a 9 mM $H_2CO_3$ solution (9 mM $Na_2CO_3$ is a popular IC eluent), the residual conductance follows a log-log relationship with the residual $H_2CO_3$ concentration; the conductance changes approximately linearly with the square root of the concentration.

For bicarbonate and/or carbonate eluents the coated asymmetric membranes of the present invention would be useful for removing the $CO_2$ from the eluent. For hydroxide or borate based eluents the devices of the present invention would be useful for removing the peak constituting to dissolved $CO_2$/carbonate in the sample. The net effect of removing the $CO_2$ peak is improved integration and quantitation and ability to tailor separations.

As set forth above, the devices of the present invention may also be useful for removing volatile components other than $CO_2$ such as electrolytic gases such hydrogen or oxygen. Other volatile components such as HCN, $H_2S$ and $NH_3$ or ethanol, methanol, acetonitrile etc could also be removed by the devices of the present invention. It is possible to collect these volatile components from the chromatographic stream using the devices of the present invention and pursue further analysis of the removed components by pursuing further chromatographic analysis or by adding a suitable detector in the receiver flow stream. Reagents that may allow detection of the removed species may also be added as per the present invention before detection.

In another embodiment, the GRD units of the present invention are used for pre-treating a liquid sample stream prior to separation of the analytes. Specifically, at least part of the volatile component(s) in the liquid sample stream is removed by flowing it out one side of a membrane in a removal device. The perm selective membrane may be of the foregoing type including at least one membrane or wall having a surface coated with a coating less than 10 micron thick on a porous host. The analytes are chromatographically separated in the sample stream from which desired components have been significantly removed and are detected by detector as described above.

In general, any of the GRD units described above may be used employed in this pretreatment mode. In addition, as described below, the volatile component removal device may comprise a liquid sample injection loop so that the sample is injected into this device which serves the dual functions of sample injection and removal of volatile components.

As set forth above, one embodiment of the GRD unit comprises a coated polymer tube of the foregoing type in a gas-removal casing. The device includes spacing around the tubing typically in the form of an annular opening. In one embodiment, the fluid typically a liquid flows in the surrounding opening and in a counter-current direction to the flow of the sample stream through the tubing. Alternatively, as set forth above, the open space surrounding the tubing may be connected to a vacuum source which draws a vacuum from one end of the opening while plugging the other end to assist removal of the gas.

Figure 14:
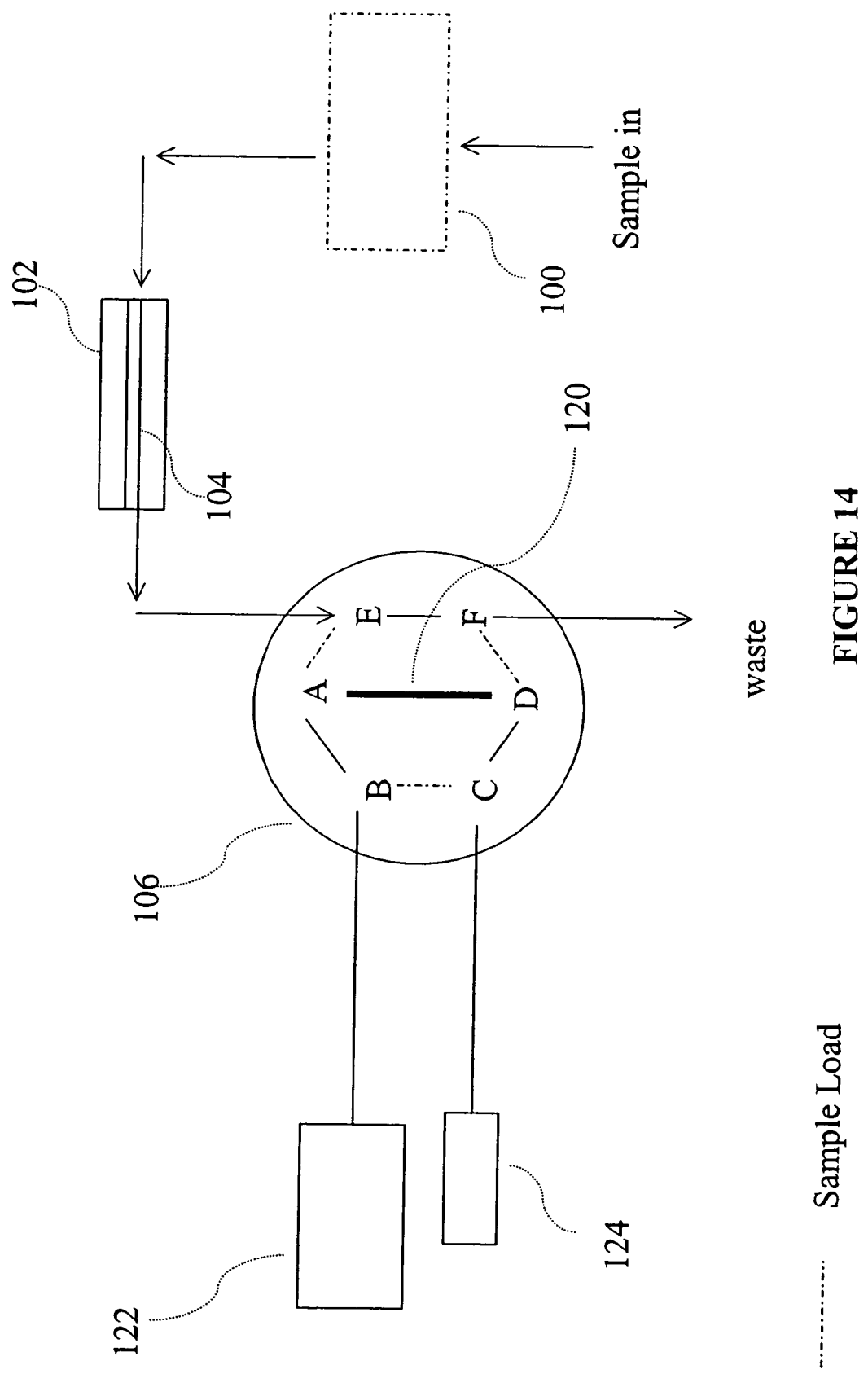

Referring to FIG. 14, one embodiment of the use of a GRD for pretreatment is illustrated which illustrates gas-removal and sample injection for a chromatography system. In general, conventional liquid chromatography or specifically ion chromatography systems may be used for the sample injection, chromatography, and detection. An exemplary system could be of the type sold by Dionex Corporation under the trademark ICS 2500.

Referring to FIG. 14, the liquid sample stream may be first directed to an optional pretreatment suppressor 100 in which the liquid sample stream is suppressed. The suppressor is upstream of GRD unit 102. The pretreatment suppressor serves to convert the desired compound to be removed to a largely unionized form which could be more easily removed by the GRD. For example, when the sample stream includes a carbonate compound, the stream may be converted to an acid form in the pretreatment suppressor for release of carbon dioxide gas which is transported across the wall of the membrane for removal from the sample stream. One reason for converting carbonate salts to the acid form and thus to create a volatile component for removal is that typically carbonate is not a tested component of the sample. Thus, by removing the carbon dioxide, the remaining sample analytes may be analyzed substantially free of interfering carbonate.

Any suppressor may be used for purposes of this pretreatment suppressor including a packed bed suppressor or a chemical or electrolytic suppressor. An electrolytic suppressor is disclosed for pretreatment of a sample stream in Stillian U.S. Pat. No. 5,597,481. As set forth in this patent, for pretreatment the suppressor serves to substantially convert the sample stream to acid or base form. Any of the suppressors disclosed in the Background portion or main specification of U.S. Pat. Nos. 5,773,615 or 6,495,371 may be employed as well.

GRD unit 102 may be of the type described above. As illustrated, the sample stream from the suppressor flows through a membrane shown as tube 104. The desired volatile component from the liquid sample stream is transported across the wall of tubular membrane 104.

The effluent from GRD unit 102 flows to a conventional six-way valve 106 and from there to chromatography column, not shown, to a conventional detector. In ion chromatography, the effluent from the column flows through a suppressor and then to a detector. In one such system, the suppressor is of the type sold by Dionex Corporation under the trademark ATLAS and the ion chromatography system is of the type illustrated in U.S. Pat. No. 6,495,371. A system of this type without the pretreatment suppressor or a GRD device is sold by Dionex Corporation under the name ICS 2000.

Referring again to FIG. 14, suitable valving for loading the sample stream effluent from GRD unit 114 to a sample loop is illustrated. Such valving is a six-port valve with the ports designated A-F. The dotted line represents sample load and the solid line represents sample inject. During sample loading of the sample loop 120, sample flow is directed through ports E, A, D, F and then to waste. At the same time, eluent may be pumped by pump 122 through ports B and C and the flow is directed in to column 124. During the sample inject mode the sample is displaced from the sample loop 120 and the flow is directed to the column. The eluent is pumped by pump 122 through ports B, A, D, C and then to chromatography column 124. At the same time, the sample stream from the GRD unit may be directed through open ports E and F and to waste.

The ionic species in the sample are separated in chromatography column 124 in accordance with well-known chromatography principles. Then, as illustrated in the '371 patent, in an ion chromatography system, the sample may be directed to a suppressor and from there to a detector, suitably a conductivity detector as is also illustrated in the '371 patent.

A concentrator column is used when the analytes of interest in the sample are at such a low concentration that it would be difficult to analyze without a preconcentration step. A suitable combination of pretreatment suppressor and concentrator column is illustrated in U.S. Pat. No. 5,597,481. In general, the concentrator column traps the ionic species of the sample in a tight band. When sufficient amount of ionic species are collected, the sample on the concentrator column is eluted in an eluent stream and directed to a chromatography column as illustrated in the '481 patent.

Figure 15:
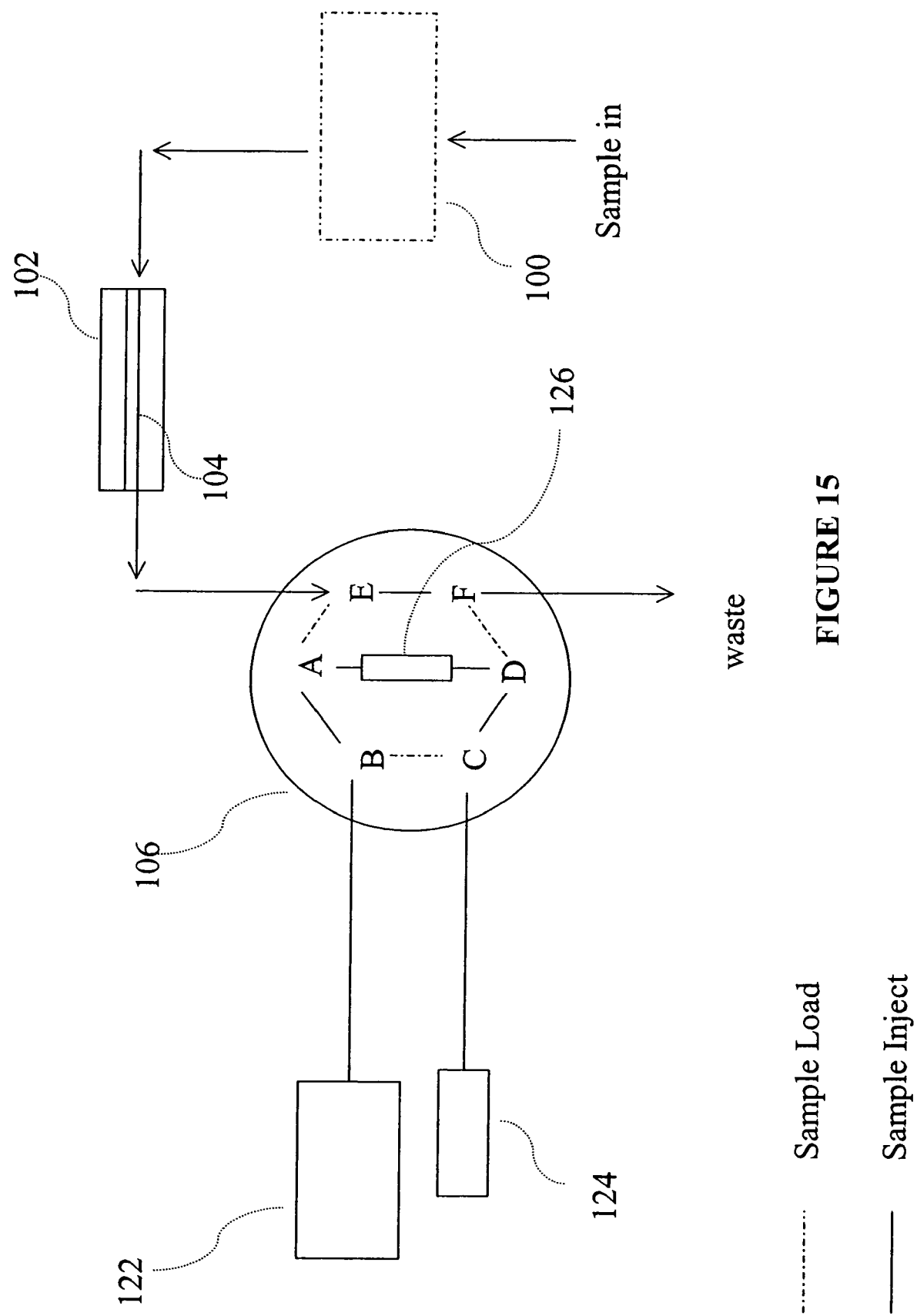

Referring to FIG. 15, a schematic representation of a system is illustrated and which is the same as that of FIG. 14 except that a concentrator column 126 is substituted for sample loop 120. Like parts are designated with like numbers. The same valve port positions as are illustrated in FIG. 14 apply to the embodiment of FIG. 15. The concentrator column performs the same function illustrated in the '481 patent. Briefly, in a concentrator column, during sample stream flow through the concentrator, analyte ions in the sample are retained in the column which may comprise an ion exchange packing or a membrane. When a sufficient amount of such ions are retained for the desired detection, the flow of sample stream through the concentrator column 126 is terminated and the eluent is pumped through the concentrator column and to the chromatography column in the manner described above.

In one embodiment, the GRD comprises at least one porous wall having a surface coated with a coating of polymer permeable to a component of interest, the coating having a thickness less than 10 micron. In another embodiment, the gas-permeable membrane may be made from an amorphous copolymer of perfluoro-2,2-dimethyl-1,3-dioxole. Such polymer material is sold by Du Pont under the trademark Teflon AF and is described in U.S. Pat. No. 4,977,008.

For ion chromatography, a suppressor is disposed between the chromatography column and the sample stream flow channel inlet in fluid communication with it. As set forth above, in a preferred GRD, a gas-removal compartment is disposed on the opposite side of the membrane wall from the sample stream flow channel. One form of pretreatment suppressor disposed upstream of the GRD is a membrane suppressor comprising a suppressor membrane. This pretreatment suppressor has a regenerant flow channel on the opposite side of the pretreatment suppressor membrane from a liquid stream flow channel. The regenerant flow channel may be in fluid communication with the gas-removal compartment of the GRD so that the liquid solution exiting the regenerant flow channel flows into the gas-removal compartment and serves as solution for removing the volatile component of interest which is transported across the GRD permselective membrane.

In another embodiment of the invention, not shown, the liquid sample injection loop is in the form of a GRD. Thus, for example, in the embodiment of FIG. 14, sample loop 120 would be a GRD and the separate GRD 102 is eliminated. Here, gas-removal is accomplished in the sample injection loop in this embodiment.

In order to illustrate the present invention, the following non-limiting examples of its practice are illustrated.

In the following non-limiting Example 1, all reagents were of analytical grade. Nanopure water was used for reagent preparation and for IC. All experiments were carried out with IC equipment from Dionex Corporation. Instrument control and data acquisition was carried out with Peaknet™ software. Elevated temperature operations were either carried out within an oven (LC-30, maintained at 30° C.) or a miniature in-line heater to heat the stripping solution.

EXAMPLES

Example 1

Construction of $CO_2$ Removal Device (GRD)

Figure 2A:
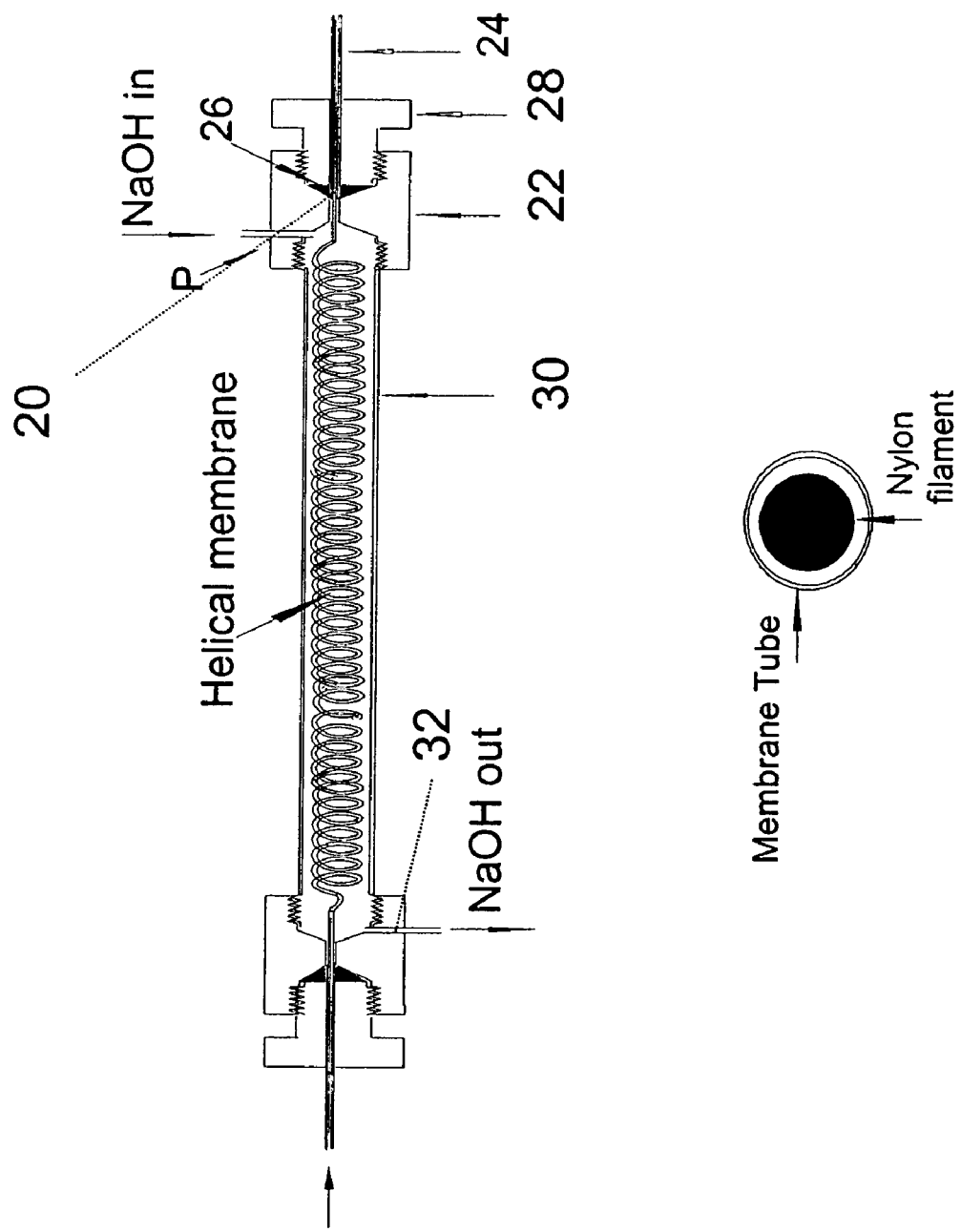
FIG. 2A is a schematic for the volatile component or GRD (gas removal device), inset shows cross-section of membrane and nylon filament; NT, nylon jacket tube; U, union; N, male nut; F, FEP tube; C, ferrule; P, PEEK tube

This example will be described with respect to FIGS. 2(a) and (b). Microporous tubular polypropylene membranes (400 µm i.d., 25 µm wall, nominal pore size 0.02 µm, surface porosity 40%, Celgard X-20, Celanese Corp., Charlotte, N.C.) were coated with silicone rubber by immersing the membrane tube in a solution of silicone rubber adhesive (Macklanburg-Duncan or General Electric, translucent type for household use) in hexane. Unless otherwise stated, the concentration was 1.5-2% (w/v). A length of the membrane tube was pulled through the solution in one direction and then pulled back in the opposite direction. The membrane was then suspended vertically and allowed to dry in a dust free enclosure for ≧4 h. The desired length of the coated membrane tube 20 was cut and a 200 µm diameter nylon monofilament (4 lb strength, STREN, duPont) was inserted in the hollow fiber, with ends of the filament protruding out of the fiber. One end of the fiber was passed through a 10-32 male-male union or fitting 22 (Dionex Corp., the union opening was drilled to enlarge the bore) and inserted into a Teflon tube segment 24 (FEP Teflon Tubing, 0.02 inch i.d. 0.062 inch. o.d., Upchurch). The tube end was sealed with a compression ferrule 26 and a 10-32 male nut 28 attached to the union. The fiber end with union-connector assembly was affixed to a small-bore steel tube 1/16 in. o.d.) with PTFE tape. The filament-filled membrane tube 20 was coiled around the steel tube and the free end was again affixed with PTFE tape. The whole assembly was immersed in boiling water for 30 min to thermoset the filament. The tapes and the helical tube assembly were then removed from the support and as shown in FIG. 2a, the assembly then enclosed in a hard nylon jacket tube 30 (0.188 inch o.d., 0.137 inch i.d., 4.5 to 5 inch length), provided at each end with 10-32 threads so it could be directly connected to union 22. 30 was further provided with inlet/outlet apertures, to which PEEK tubes 32 (0.03 inch i.d., 0.062 inch o.d., Upchurch) were connected and epoxied in place. These provided for flow of the external fluid. The free terminal end of the membrane tube was now sealed in the same manner as the first end. In some cases the inlet/outlet aperture for the external fluid was provided directly in the fitting 22 by drilling it appropriately.

A 200 µm i.d. microporous polypropylene membrane, containing a 3-4 micron thick layer of plasma-polymerized disiloxane was obtained from Neomecs (Eden Prairie, Minn.). The complete device was made the same way as the previous description, except without further silicone coating or inserted filaments. Terminal Teflon tubes used for connection were 0.3 mm in i.d.

Unless otherwise noted, a GRD based on an 80 cm long Celgard membrane tube singly coated with a 1.5% silicone rubber solution was used and was placed between the suppressor and the detector. Except as stated, the eluent flow rate was 0.4 and 1.0 mL/min for 2 and 4 mm columns, respectively, with 100 mM NaOH solution pumped peristaltically or pneumatically at ~ 0.5 mL/min on the exterior flow channel of the GRD. In some experiments, the suppressor waste (in the case of a hydroxide eluent IC) was used as the sink solution. Elevated temperature operations were either carried out within an oven (LC-30, maintained at 30° C.) or a miniature in-line heater (vide-infra) to heat the stripping solution.

In-Line Heater

Figure 2B:
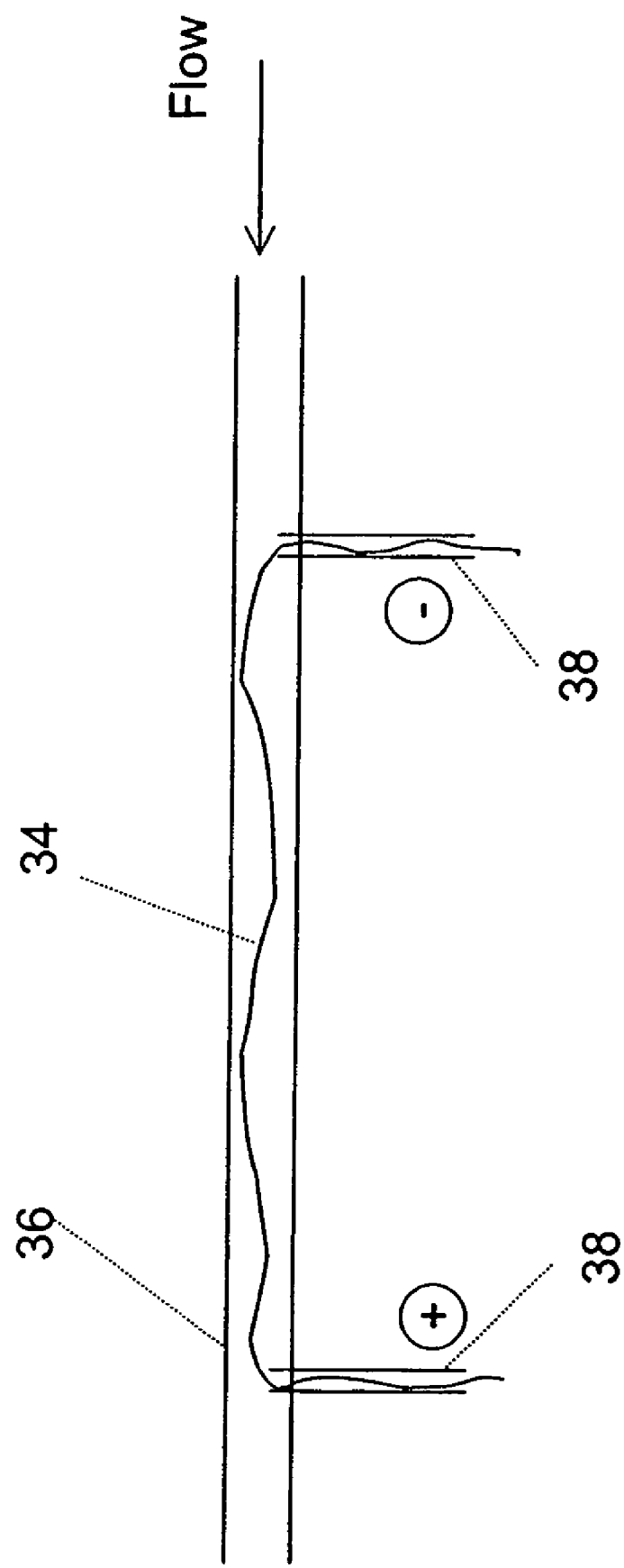
FIG. 2B is an inline heater; P, PEEK tube; SS, stainless steel tube; NiCr, nichrome wire; +−, power connections.

An in-line heater that directly heats the influent stripping solution was constructed similar to a heater design described in Dasgupta et al., *Anal. Chem.* 2003:75, 3924-3928. A 40-ga. nichrome wire 34 was inserted through a PEEK tube 36 (0.03×1/16×5 inch long) and the ends were sealed by segments of hypodermic stainless steel tubing with epoxy adhesive put in at the ends to avoid leakage (FIG. 2b). Excess nichrome wire was trimmed off. A variable voltage DC power supply was used to apply voltage to the two steel tube termini 38 that also functioned as liquid inlet/outlet. Up to a maximum of 10 V was applied, leading to ~4 W of dissipated power. If the heated external solution (0.5 mL/min) is in thermal equilibrium with the internal solution (1.0 mL/min) and the system were adiabatic, the overall temperature rise will be ~40° C. In practice, there was large heat losses at the low flow rates involved. The exit temperature of the liquid from the heater was ~72° C. but decreased to 54° C. by merely the 10 cm passage to the GRD inlet. The measured GRD lumen outlet temperature was only 10° C. above the lumen inlet temperature. The majority of subsequent experiments were conducted by incorporating the GRD within an oven.

RESULTS AND DISCUSSION

Effect of the Silicone Coating Thickness

Figure 3:
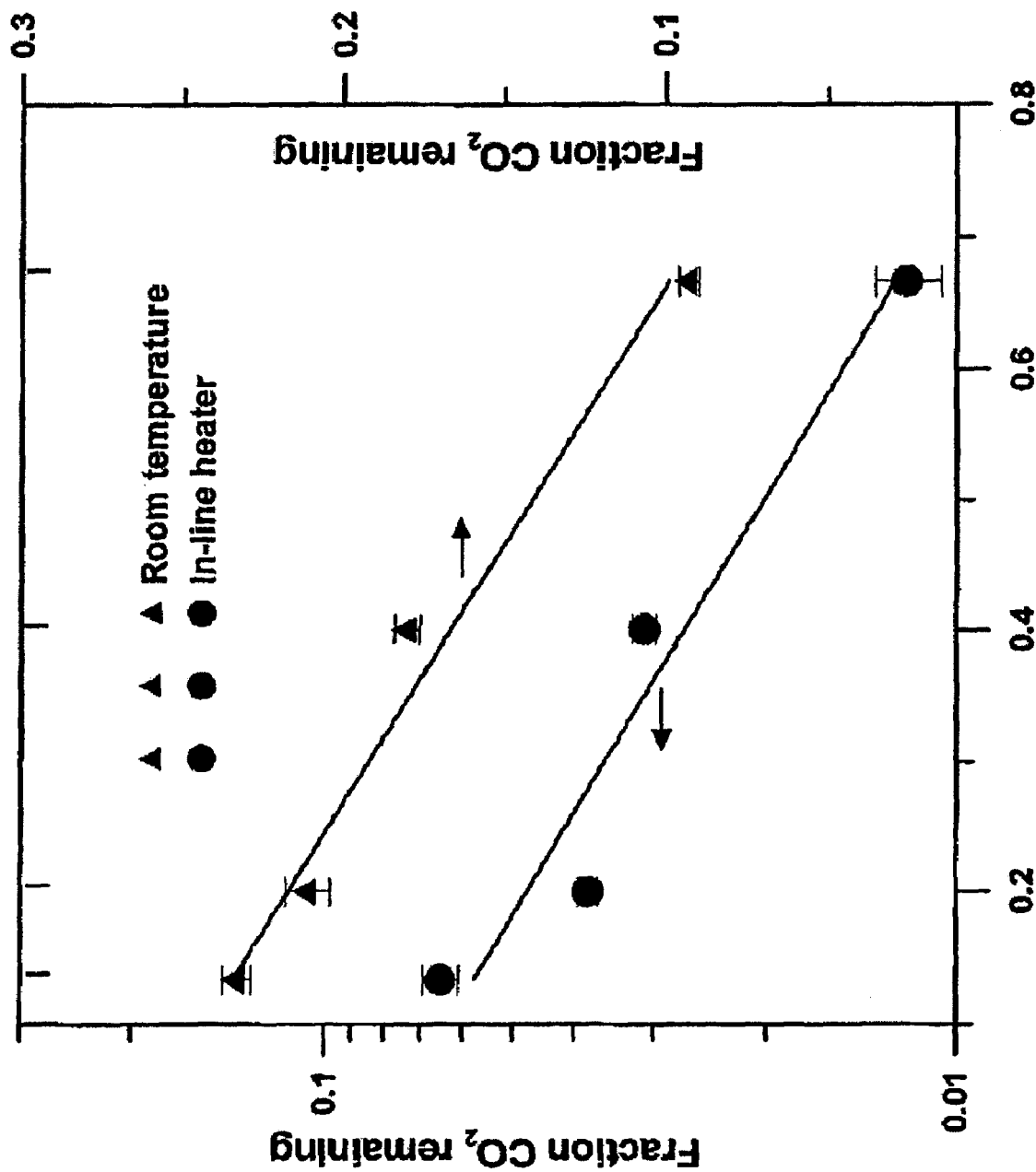
FIG. 3 illustrates residual $CO_2$ as a function of the silicone rubber content of the coating solution with the device operated at room temperature (right, linear ordinate) and with an in-line heater (left logarithmic ordinate). The coating thickness was measured to be 1.4 µm for the 1.5% silicone rubber coating solution and is assumed to be linearly proportional to the coating solution concentration.

FIG. 3 shows the fraction of $CO_2$ that remains as a function of the amount of silicone rubber in the coating solution both at room temperature and with the in-line heater (4 W). As a first approximation, we assume that the thickness of the coating is directly related to the concentration of the silicone rubber in the solution. For the relatively short membrane tube length used in this experiment, the fractional removal efficiencies (f) are low. Under these conditions, the transport to the membrane is not the limiting factor and transport through the membrane, related to the reciprocal thickness of the transport layer, may become the dominant factor. Accordingly, (1-f), the residual fraction of $CO_2$, is approximately linearly related to the reciprocal thickness. At elevated temperatures, however, removal is much more efficient and log(1-f), rather than 1-f shows a better linear relationship with 1/t, suggesting that mass transport to the membrane becomes the limiting factor.

The least amount of silicone used in the coating solution (1.5%) led to the best removal efficiencies (91% and 99% in the cold and heated modes respectively). We also found that the membranes coated in this manner are not always free of pinhole leaks. The extent and frequency of occurrence of such leaks increases with decreasing silicone content of the coating solution and with the prescribed coating regimen, 1.5% silicone content of the coating solution was a practical lower limit. This was therefore used henceforth. At a flow rate of 1 mL/min, the backpressure induced by the GRD itself plus the detector cell and the postdetector exit tubing was 38 psi (~70% of this was contributed by the detector cell and associated tubing). The maximum liquid leakage observed through membrane pinholes under this condition was 1±0.1 µL/min, with no fluid flow exterior to the membrane (this required 10-12 h collection with the outer jacket closed and may even contain contributions from permeation of water vapor and recondensation in the jacket). As long as there is a significant positive pressure differential between the interior of the membrane and outside, external liquid leakage into the lumen did not occur and the observed degree of leakage, amounting to 0.1% of the original flow, presents no practical issues. With a flow of 1 mL/min, the Neomecs 200 μm i.d. membrane was used in a maximum length of 50 cm; the head pressure on such a GRD (plus detector etc) was 60 psi. There was no observable liquid leakage with this membrane.

Microscopy

Figure 4A:
FIG. 4 are scanning electron photomicrography: (a) uncoated membrane-outer surface, scale bar 0.5 µm; (b) coated membrane-outer surface, scale bar 0.5 µm; (c) coated membrane cross section, scale bar 50 µm; (d) commercial Neomecs membrane, scale bar 2 µm.
Figure 4B:
Figure 4C:
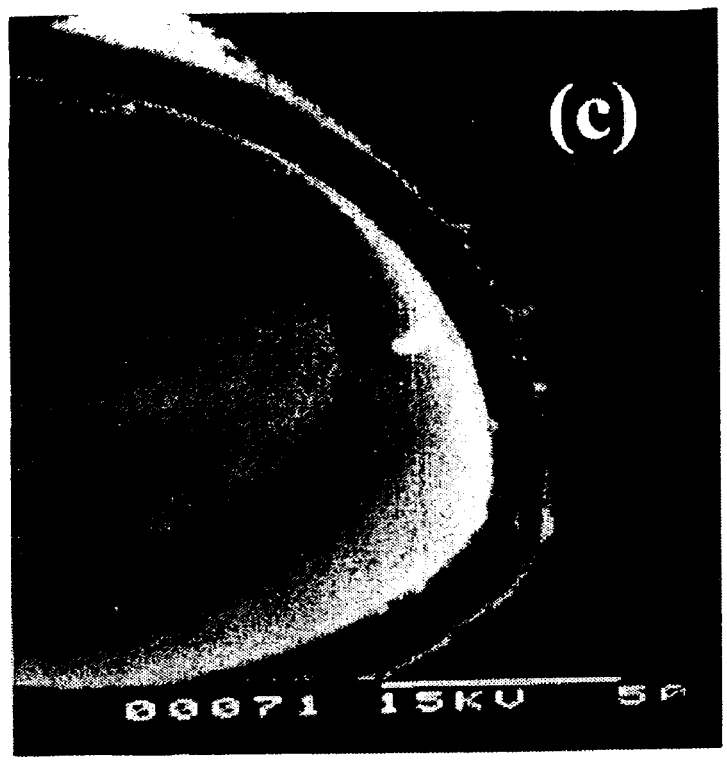

Scanning electron micrographs of the membranes show the exposed pores in the uncoated membrane (FIG. 4a). while the silicone coating covers most of the membrane surface in the coated membrane (FIG. 4b). Microscopic measurements of the wall thickness indicated that the coated membrane wall is ~1.4 μm thicker than the virgin membrane. The internal surface roughness is evident even in the relatively low magnification cross sectional image of the coated tube (FIG. 4c) and the image also suggests that the coating is present on both sides. This is consistent with the fact that the hexane solution of silicone rubber is seen to readily wet the membrane. With a density of 1.15 and a measured 3% volatile content of silicone rubber adhesive, a 40-50 μm thickness of the liquid film (per passage of the membrane through the coating solution for each of two passages) is sufficient to produce the observed film thickness for a coating solution containing 1.5-2% silicone rubber.

Figure 4D:
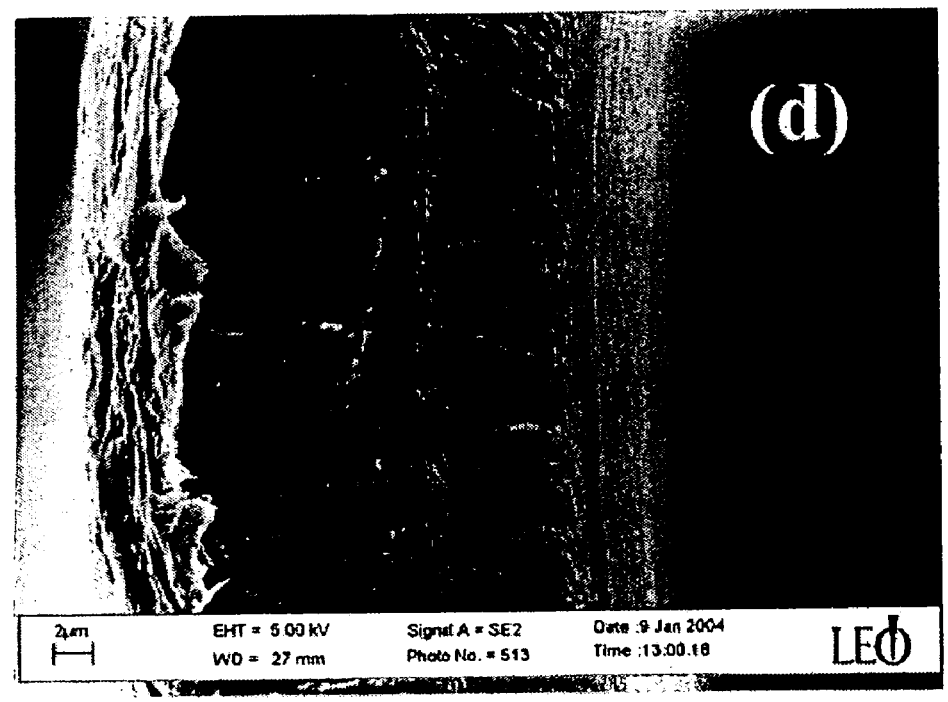

The manufacturer of the commercial disiloxane coated membrane does not specify the thickness of the disiloxane layer. With a stated effective permeability of $8.36 \times 10^{-4}$ cc /(cm$^2$.s.cm Hg) the known permeability of 4550 barrers for silicone rubber (this is for poly(dimethylsiloxane) and may not be exactly true for disiloxane), one estimates a barrier layer thickness of 5.4 μm. The cross sectional image of the membrane tube (FIG. 4d), suggests a coating thickness of 3-4 μm, consistent with this estimate.

Effect of Membrane Fiber Length and Temperature

Figure 5:
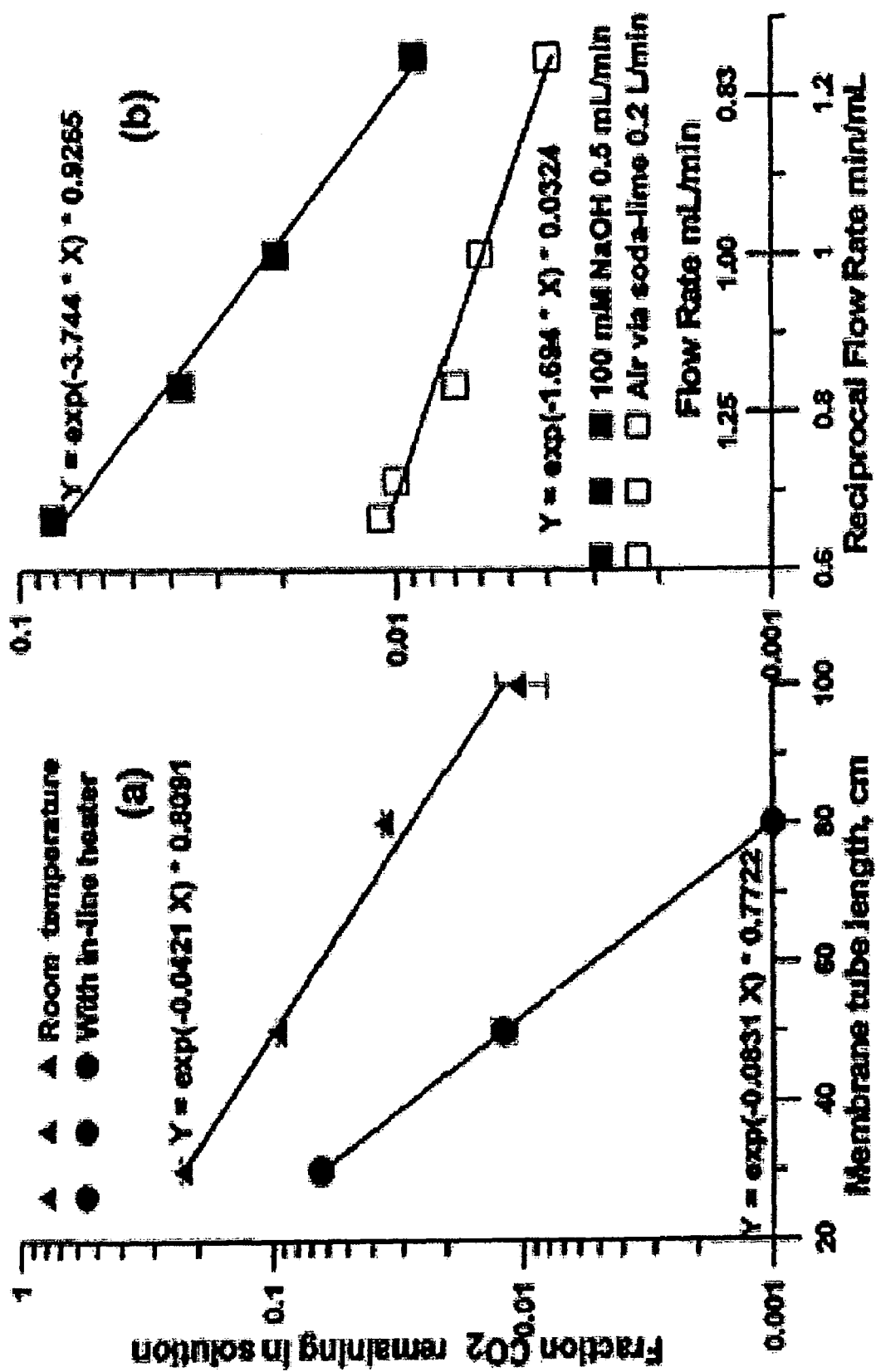
FIG. 5 is a Gormely-Kennedy plot of the residual $CO_2$ as a function of (a) the tube length at room temperature and at 32° C. and (b) as a function of the lumen flow rate (80 cm GRD) with air or 100 Mm NaOH flowing in the jacket.

FIG. 5 shows the effect of the tube length on the $CO_2$ removal efficiency. Removal as a function of length follows a linear relationship between the logarithm of the fraction remaining and the length of the tube as predicted by the Gormley-Kennedy equation. (Gormley et al., *Proc. Roy. Ir. Acad. Sci.* Sect. A 1949, 52, 163-169.) The 80 cm long tube removed ~97% of the $CO_2$ at room temperature and essentially quantitatively ($\geq$99.9%, it is very difficult to measure the exact removal efficiency at these high efficiencies) with the in-line heater. The difference in the two temperatures (22° C. vs 32° C.) causes approximately a doubling of the slope of the ln(1-f) vs. length plot. If the Stokes-Einstein relationship adequately defines the liquid phase diffusion coefficient and we consider that the temperature change results in a factor of 1.25 change in the viscosity, the temperature change will result in a 1.3× change in the diffusion coefficient (which appears in the exponent in the Gormley-Kennedy expression) thus assisting mass transfer to the membrane. There are other aspects of $CO_2$ removal that are assisted by an increase in temperature. It is $CO_2$ and not $H_2CO_3$ that permeates (dissolves in and then diffuses out through the membrane. $H_2CO_3$ must dehydrate to $CO_2$; this process is not instantaneous. Based on literature data, and assuming Arrhenius behavior, the rate constant of the dehydration process will increase from 19.4 s$^{-1}$ at 22° C. to 47.2 s$^{-1}$ at 32° C. With a typical residence time of $\geq$4.5 s in the GRD, the dehydration rate is likely not a major factor. The pressure differential between the two sides of the membrane that drives the removal process. Since exterior pCO$_2$ is ~zero, the motive force is directly related to the interior pCO$_2$. Based on available thermodynamic data, the Henry's law solubility of $CO_2$ decreases by a factor of 1.3 between 22° C. and 32° C. Finally, an increase in temperature also aids the diffusive transfer of $CO_2$ across the membrane.

$CO_2$ Removal Efficiency Exhibit by Different GRD's

Since elevated temperature operation was clearly advantageous, further experiments were conducted with the GRD located in the chromatographic oven maintained at 30° C. Table 1 shows the results for different GRD units at room temperature and at 30° C. It is interesting to note that the uncoated membrane performs slightly worse than the coated membrane, especially at elevated temperatures. As previously noted, a mass transfer limiting step with a conventional microporous membrane is the formation of a stagnant liquid film within the micropores. With both sides of the membrane coated, this possibility is obviated. In either case, it is not possible to operate over a continued period with uncoated membranes because of serious leakage. Although a 50 cm long 200 μm i.d. Neomecs membrane does not provide quantitative removal for $CO_2$ at 1 mL/min, since Gormley-Kennedy behavior is obeyed (see below), such a device is expected to remove 99.5 and 99.97% of the $CO_2$ at flow rates of 0.5 and 0.25 mL/min at 30° C. respectively. The comparison between a 50 cm 400 μm Neomecs device and a coated Celgard device, made in an identical filament filled manner, shows that the room temperature performance of both devices to be the same but at elevated temperature, the coated Celgard device performs perceptibly better.

TABLE 1

Carbon dioxide removal by different $CO_2$ removal devices

| Tubing | Membrane dimension Length, cm | Membrane dimension I.D., mm | Nylon filament dia. Mm | Silicone coating | % $CO_2$ removal, 22° C. | % $CO_2$ removal, 30° C. |
|---|---|---|---|---|---|---|
| Celgard | 50 | 0.4 | 0.2 | No | 91.4 ± 0.1 | 95.3 ± 0.8 |
| Celgard | 50 | 0.4 | 0.2 | Yes | 91.5 ± 0.3 | 96.6 ± 0.6 |
| Celgard | 80 | 0.4 | 0.2 | Yes | 95.4 ± 0.1 | 98.6 ± 0.3 |
| Celgard | 80 | 0.4 | 0.2 | Yes | 95.9 ± 0.1 | 97.8 ± 0.1 |
| Celgard | 100 | 0.4 | 0.2 | Yes | 97.7 ± 0.2 | 99.4 ± 0.2 |
| Neomecs | 50 | 0.2 | N/A | N/A | 81.8 ± 0.5 | 90.5 ± 0.8 |
| Neomecs | 50 | 0.4 | 0.2 | N/A | 91.5 ± 0.1 | 92.9 ± 0.2 |

Lumen flow 1 mL/min;
Sink solution: 100 mM NaOH at 0.5 mL/min.

Options for Removing $CO_2$ and the Effect of Lumen Flow Rate

Table 2 shows the results of using different options external to the membrane for removing $CO_2$ from the eluent stream. Gas flow is superior to a liquid sink, presumably because diffusion limitations are less. Using soda-lime treated air flow, one of the best options, as well as 100 mM NaOH (used as the benchmark sink for all tests), the removal efficiencies as a function of the lumen flow rate are shown in FIG. 5b. Again, Gormley-Kennedy behavior is observed.

TABLE 2

Performance of different $CO_2$ removal options external to the membrane[a]

| Fluid Flow mode at outside channel of GRD | Flow rate, mL/min | % $CO_2$ removal |
|---|---|---|
| Pressurized Nitrogen | 200 | 99.2 ± 0.1 |
| Nitrogen with inline soda-lime cartridge | 200 | 99.3 ± 0.1 |
| Pump suction | 200 | 99.2 ± 0.1 |
| Pump suction with soda-lime cartridge at the inlet | 200 | 99.3 ± 0.1 |

TABLE 2-continued

Performance of different
$CO_2$ removal options external to the membrane[a]

| Fluid Flow mode at outside channel of GRD | Flow rate, mL/min | % $CO_2$ removal |
|---|---|---|
| Pressurized air | 200 | 99.3 ± 0.1 |
| Pressurized air with inline soda-lime cartridge | 100-500[b] | 99.4 ± 0.1 |
| Vacuum (pump suction with inlet restriction) | 200 | 99.1 ± 0.1 |
| Vacuum (pump suction with inlet restriction plus soda-lime cartridge) | 200 | 99.3 ± 0.1 |
| Water | 1 | 42.3 ± 2.0 |
| 50 mM NaOH | 1 | 96.9 ± 0.1 |
| 100 mM NaOH | 1 | 97.8 ± 0.1 |
| Suppressor waste | 1 | 95.8 ± 0.6 |

Figure 6:
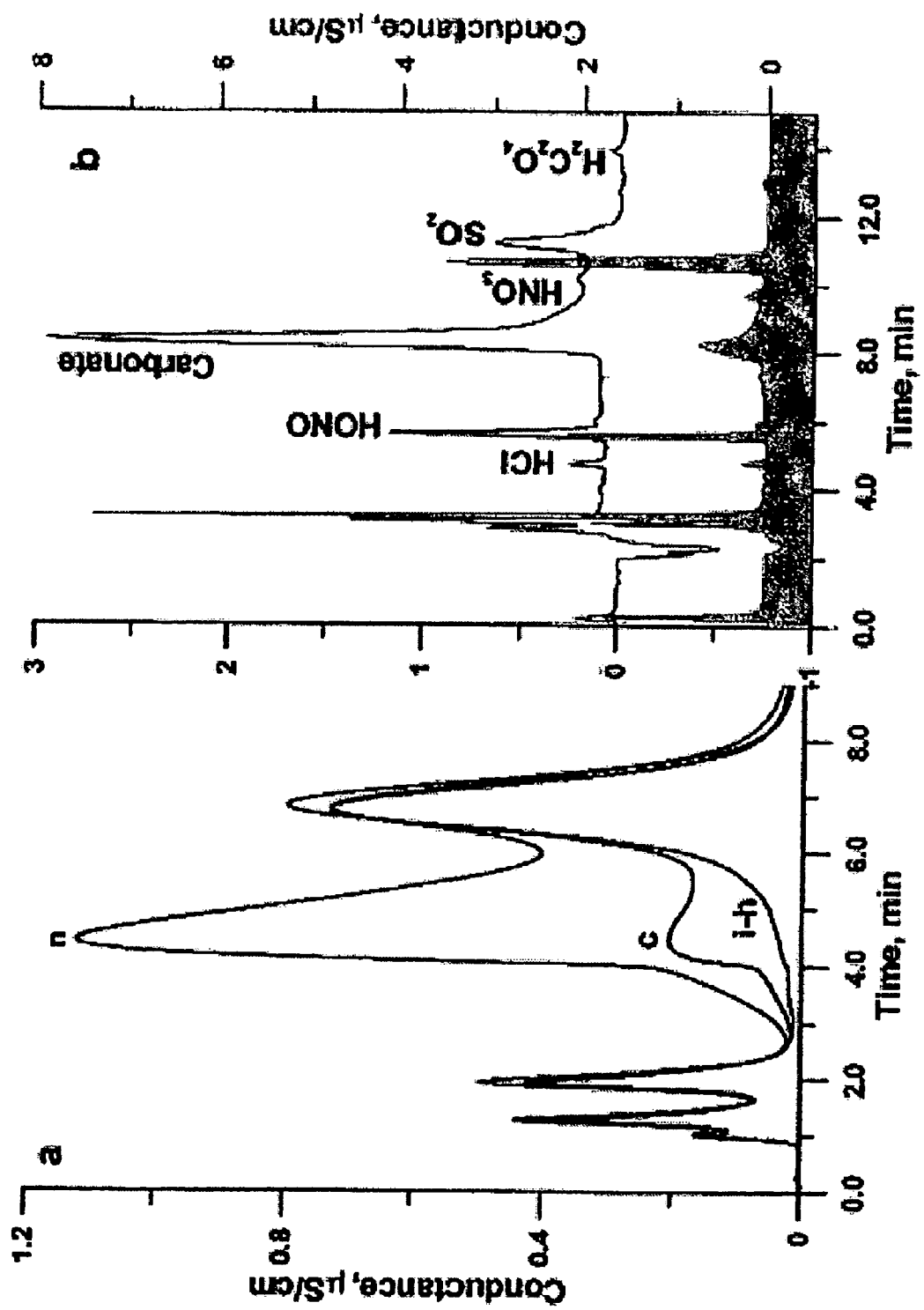
FIGS. 6(*a*) and 6(*b*) illustrate removal of $CO_2$ present in samples in hydroxide eluent chromatography (a) 4 mm TAC LP-1+AG-11 HC columns, 2 mM electrogenerated KOH at 1 mL/min, ΔP=450 psi (includes 150 psi drop prior to columns), 35 µL sample containing 150 µg/L $Cl^-$, 770 µg/L $NO_3^-$, 74 mg/L $CO_3^{2-}$ and 3.1 mg/L $SO_4^{2-}$ injected; n, no GRD, c, GRD at room temperature; i-h, in-line heater with GRD and (b) 4 mm AG11+AS11 columns, electrogenerated KOH eluent, 30° C. in LC-30 oven, atmospheric gas sample at Sydney, Fla., collected at 5 L/min and preconcentrated for 15 min. Line trace (left ordinate): 15.5 mM KOH @ 1.5 mL/min, no GRD, 16 ppt HCl, 160 ppt HONO, 40 ppt $HNO_3$, 90 ppt $SO_2$, 8 ppt $H_2C_2O_4$; solid shade (right ordinate): 17.5 mM KOH @ 1.4 mL/min, GRD at 30° C. 40 ppt HCl, 410 ppt HONO, 85 ppt $HNO_3$, 510 ppt $SO_2$, 13 ppt $H_2C_2O_4$.

[a]80 cm GRD; Lumen Flow 1 mL/min; Eluent 9.0 mM $Na_2CO_3$; Oven at 30° C.
[b]there is no difference in removal efficiency in this flow rate range Performance
Isocratic Elution
Removal of $CO_2$ from the Sample Stream This aspect concerns one of our primary interest in $CO_2$ removal—to facilitate field atmospheric measurements. FIG. 6a shows the important role a GRD can play in devising a simple relatively low pressure (450 psi) separation scheme that attempts to measure the two most important ions of interest in atmospheric measurement, nitrate and sulfate. The nitrate and sulfate content are equivalent to 0.25 ppb $HNO_3$ and 0.43 ppb $SO_2$ that will be collected in a 15 min 5 L/min sample as described in Boring et al., Anal. Chem. 2002:74, 1256-1268. Chromatography is conducted with a very low concentration of hydroxide that allows nitrate to elute long before carbonate (the amount of which in this sample is much less than that would be encountered in the real atmospheric sample, see FIG. 6b). The difference in having and not having a GRD here is whether or not sulfate can be quantitated at all. FIG. 6b shows two actual field chromatograms, one without a GRD and the other with a GRD obtained under comparable conditions; in the latter case, it was possible to use a slightly higher eluent concentration and a lower eluent flow rate because of the drastic reduction in the carbonate peak. The difficulty of quantitating low levels of $HNO_3$ without the GRD (even after optimizing the elution time difference between carbonate and nitrate under the available total elution time constraints), and the very significant improvement in the presence of the GRD is evident. It is also worthwhile to note that the quality of the water (especially with regard to its $CO_2$ content) can rarely be controlled in field work. As a result, even with an electrodialytically generated hydroxide eluent, the water dip is visible and is significantly reduced with the GRD.

Figure 7:
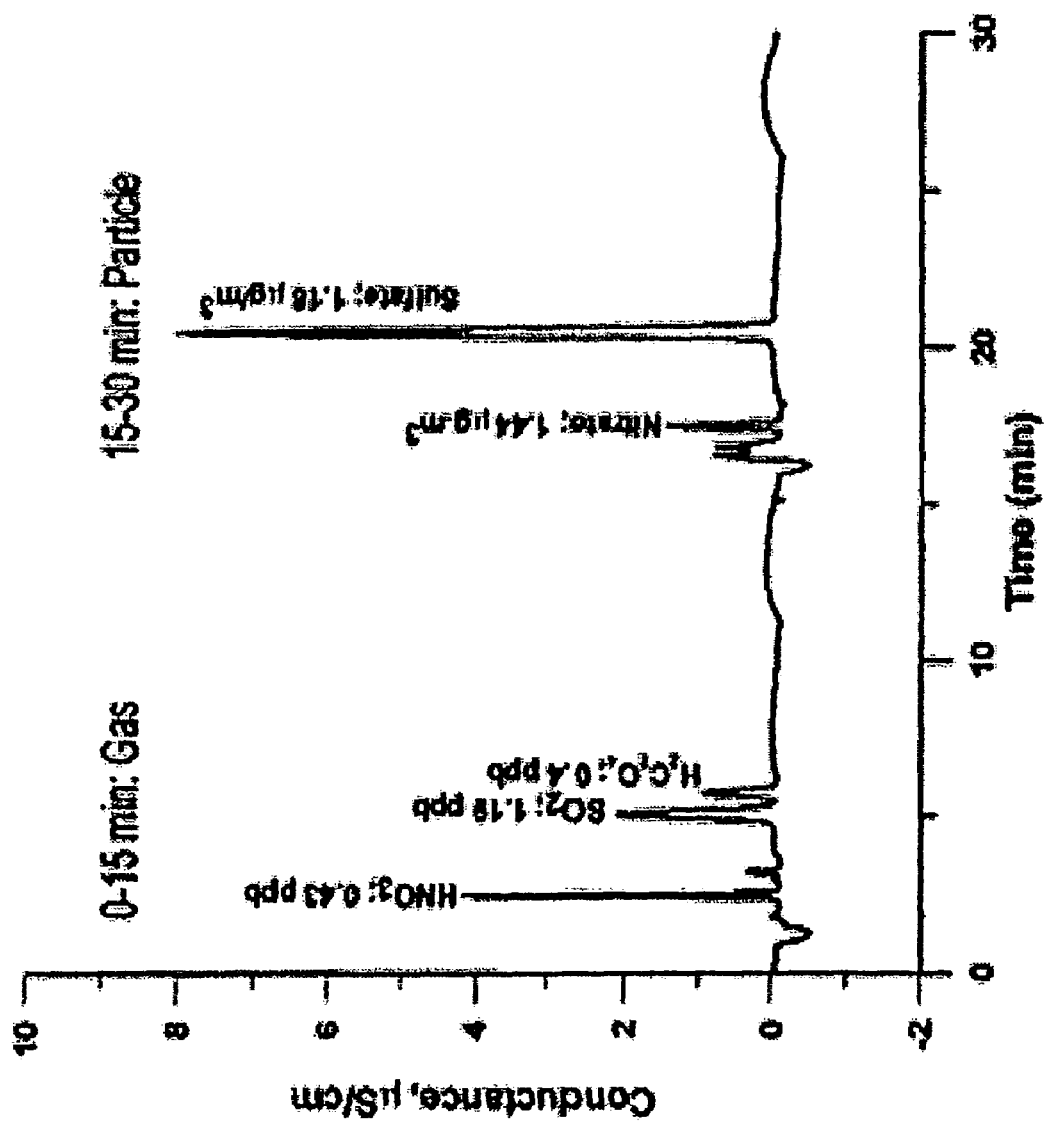
FIG. 7 are automated sequential chromatograms of collected gas and aerosol samples (see, e.g., ref. 37), with 2.4 mM $Na_2CO_3$ and 2.3 mM $NaHCO_3$, eluent 4×150 mm AG11 column, 1.0 mL/min, GRD, oven at 30° C.

The GRD permits the use of a carbonate eluent in a relatively low pressure system in field atmospheric measurements without any major sacrifice in sensitivity. The low system pressure contributes to lower maintenance. FIG. 7 shows a chromatogram from atmospheric samples from an instrument situated at a rural location in Bondville, Ill., similar in design to that described in Genfa et al., Atmos. Environ. 2003:37, 1351-1364 but with a carbonate eluent and a GRD. This instrument alternately measures gaseous and particulate constituents and has been operated with a single GRD for over a year.

Carbonate Eluents. Improvement of Detection Limits and Linearity

The GRD can significantly improve limits of detection (LODs) with carbonate eluents (Table 3). LODs were calculated on the basis of three times the standard deviation of a standard with a concentration near the LOD. Improvements are observed across the board for the test ions. Fast eluting ions such as fluoride that elute very close to the water dip cannot be detected at all from low level standards in the absence of a GRD. These LODs are expected to improve further with the use of an oven. It is of interest to compare these LODs with what can be attained by a hydroxide eluent system. However, it would be extremely difficult to cover this entire suite of analytes with an isocratic hydroxide eluent in a reasonable period, so we have used (a) a standard mixture without phosphate with isocratic elution under otherwise identical sample size and column dimensions and (b) a gradient hydroxide elution scheme with all seven ions using a 4 mm column (due to the availability of columns and equipment) and a smaller injection volume that is typical of today's state of the art practice. The LODs attained with the carbonate system with the GRD are respectable.

TABLE 3

Detection limits of common ions, ppb

| | $F^-$ | $Cl^-$ | $NO_2^-$ | $Br^-$ | $NO_3^-$ | $PO_4^{3-}$ | $SO_4^{2-}$ | |
|---|---|---|---|---|---|---|---|---|
| Test Concn ppb | 10 | 10 | 20 | 50 | 50 | 100 | 50 | |
| Carbonate, no GRD[a] | | 3.8 | 3.4 | 8.3 | 5.8 | 25.0 | 14.4 | n = 13 |
| Carbonate, GRD #31[b] | 0.7 | 2.2 | 2.4 | 3.2 | 3.4 | 15.0 | 3.5 | n = 12 |
| Gradient hydroxide[c] | 0.7 | 2.6 | 1.3 | 2.7 | 3.8 | 10.3 | 7.8 | n = 10 |
| Isocratic hydroxide[d] | 0.7 | 1.4 | 1.0 | 0.7 | 0.6 | nd[e] | 0.8 | n = 12 |
| Test Concn ppb | 5 | 5 | 10 | 25 | 25 | 50 | 25 | |
| Carbonate, GRD #31[b] | 1.0 | 2.3 | 1.3 | 3.5 | 1.9 | 5.8 | 2.4 | n = 14 |
| Isocratic hydroxide[d] | 1.2 | 3.3 | 1.2 | 1.1 | 0.9 | nd[e] | 1.2 | n = 12 |

Figure 8:
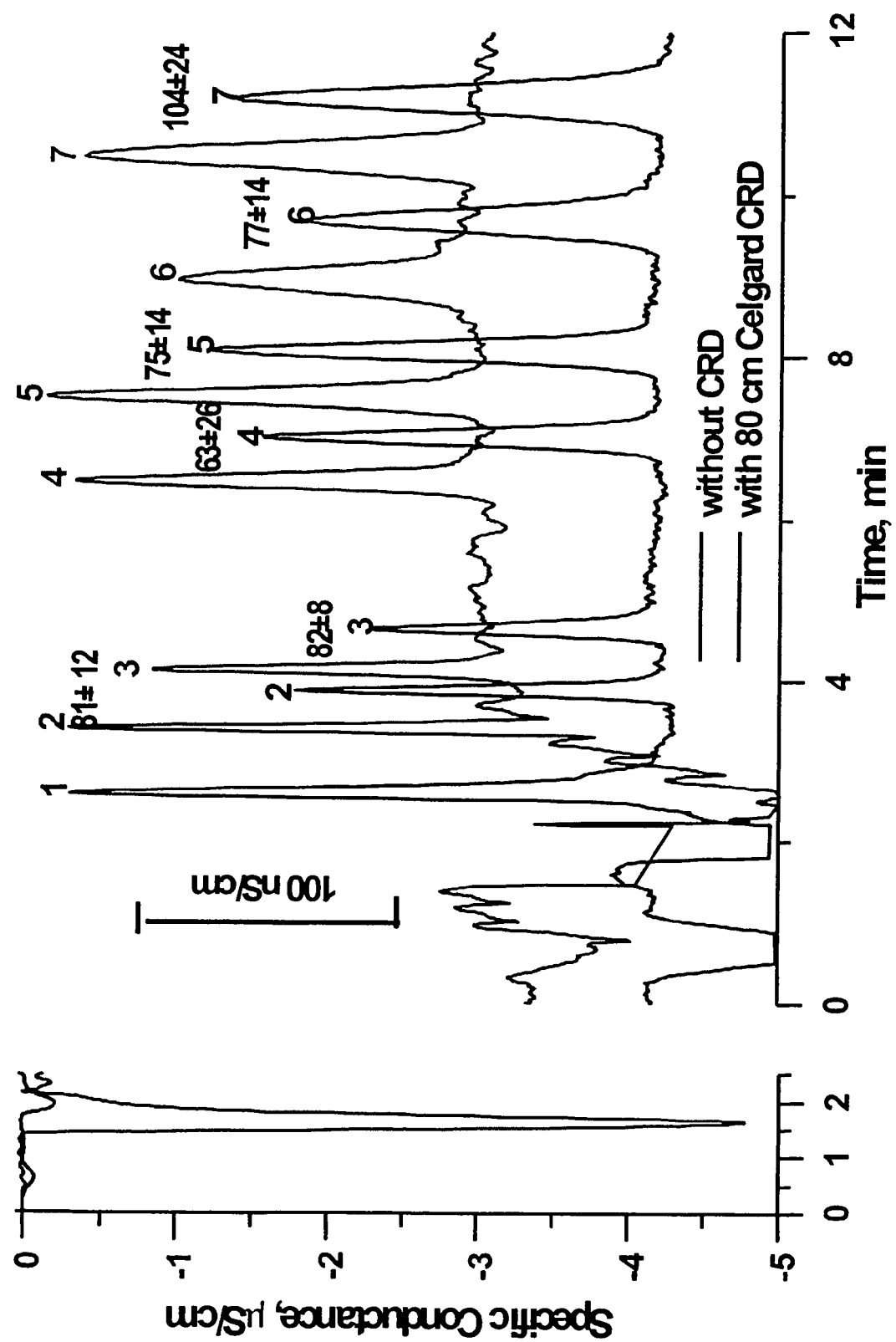
FIG. 8 is an isocratic carbonate-bicarbonate elution with performance near the LOD. 2 mm AG12/AS12, 0.3 mM $NaHCO_3$, 2.7 mM $Na_2CO_3$, 0.4 mL/min, 2 mm ASRS-Ultra, 50 mA recycle mode, Background 13.6-14.4 µS/cm without GRD (light trace), 0.90-0.96 µs/cm with GRD at room temperature (dark trace), 100 µL injections of 10 µg/L $F^-$, 10 µg/L $Cl^-$, 20 µg/L $NO_2^-$, 50 µg/L $NO_3^-$, $Br^-$, 50 µg/L $NO_3^{31}$, 100 µg/L $PO_4^{3-}$, 50 µg/L $SO_4^{2-}$. The left panel shows the dramatic difference in the water dip. The computed band dispersion (uncertainty in parentheses, n=3) is shown on top of each GRD peak in the right panel. Fluoride at this level cannot be detected without the GRD.

[a]2 mm AG12/AS12, 0.3 mM $NaHCO_3$, 2.7 mM $Na_2CO_3$, 0.4 mL/min, 2 mm ASRS-Ultra, 50 mA recycle mode, room temperature operation (no oven), background 13.6-14.4 µS/cm, 100 µL injection
[b]As in a, except GRD 31 (80 cm silicone coated Celgard) at room temperature (no oven), background 0.90-0.96 µS/cm.
[c]4 mm AS17/AG17; CR-ATC; 1.5 mL/min; 50 µL injection; 1 to 35 mM electrogenerated KOH gradient, in oven at 30° C.
[d]2 mm AS18, 20 mm electrogenerated KOH, all other conditions identical to a, no oven.
[e]not determined, does not elute in 10 min Overlaid isocratic carbonate eluent chromatograms, carried out under the conditions described in Table 3, with and without a GRD, are shown in the right part of FIG. 8. The left inset shows the vast improvement in the water dip that is observed in the presence of a GRD. As the chromatograms indicate, the additional dispersion induced by the GRD is minor. Band dispersion, defined as $(W_{1/2}^2-W'_{1/2}^2)^{1/2}$ where $W$ and $W'_{1/2}$ are the half band volumes of analyte peak with and without the GRD, are indicated for each peak in µL with uncertainties (n=3). For the majority of the analytes shown in FIG. 8, the peak area actually increased with the use of the GRD, the peak area for phosphate increasing by 12%. The enhanced sensitivity is directly traceable from the removal of $CO_2$ and the associated pliant baseline.

Figure 9:
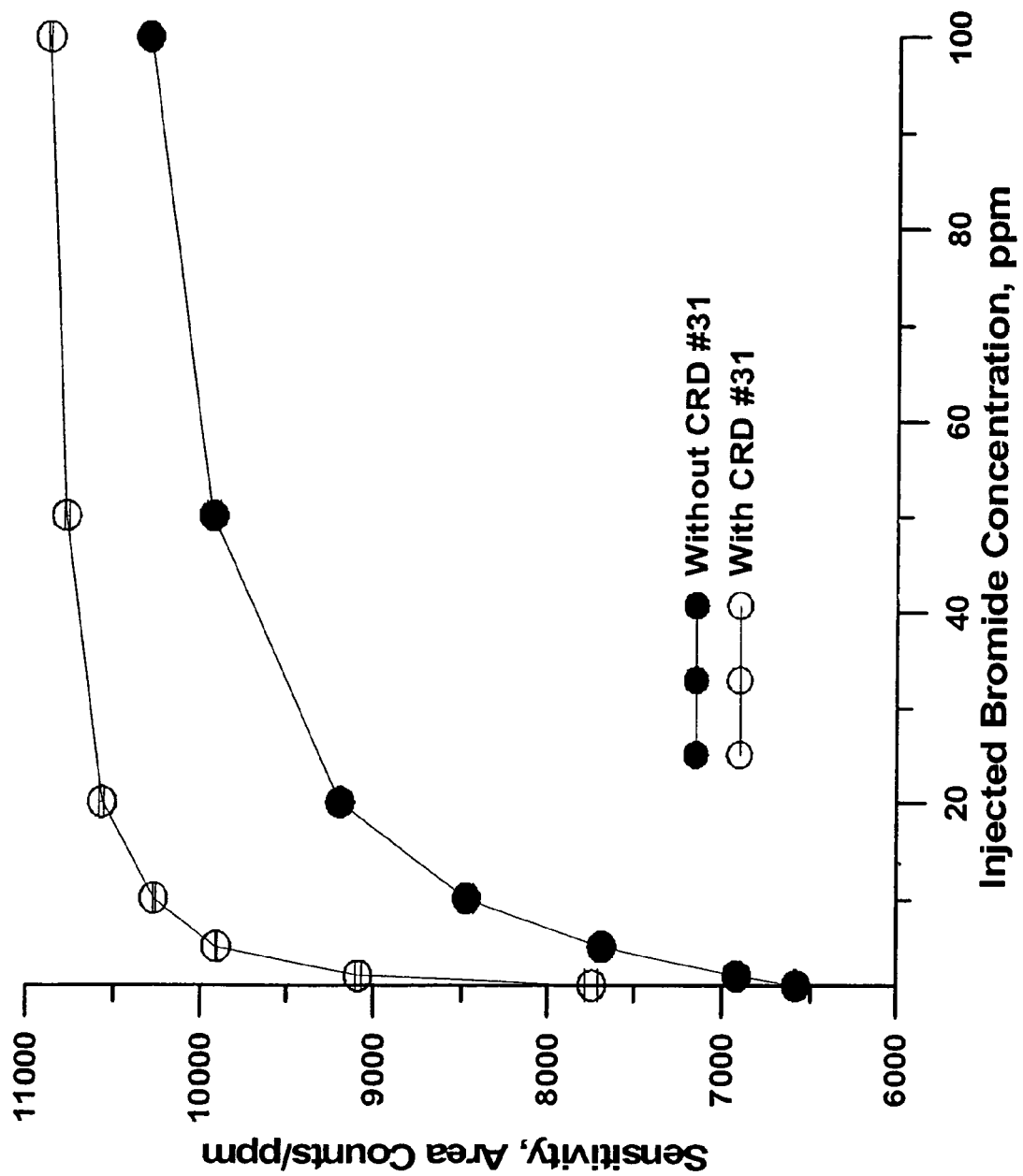
FIG. 9 is a Cassidy linearity plot for a carbonate eluent for bromide, an analyte ion of intermediate retention in the most common concentration range of 1-100 ppm. Same conditions as FIG. 8. The background was 0.6 µS/cm with GRD.

The linearity of response is best examined with a Cassidy plot (Cassidy et al., *LC·GC Mag.* May 1992, 10, 692-696), as shown in FIG. 9. The sensitivity with the GRD is higher and it reaches a constant value faster than without it. Theory predicts that at even higher concentrations, the sensitivity of the two will eventually be the same.

Bicarbonate Carbonate Gradient Chromatography

Figure 10:
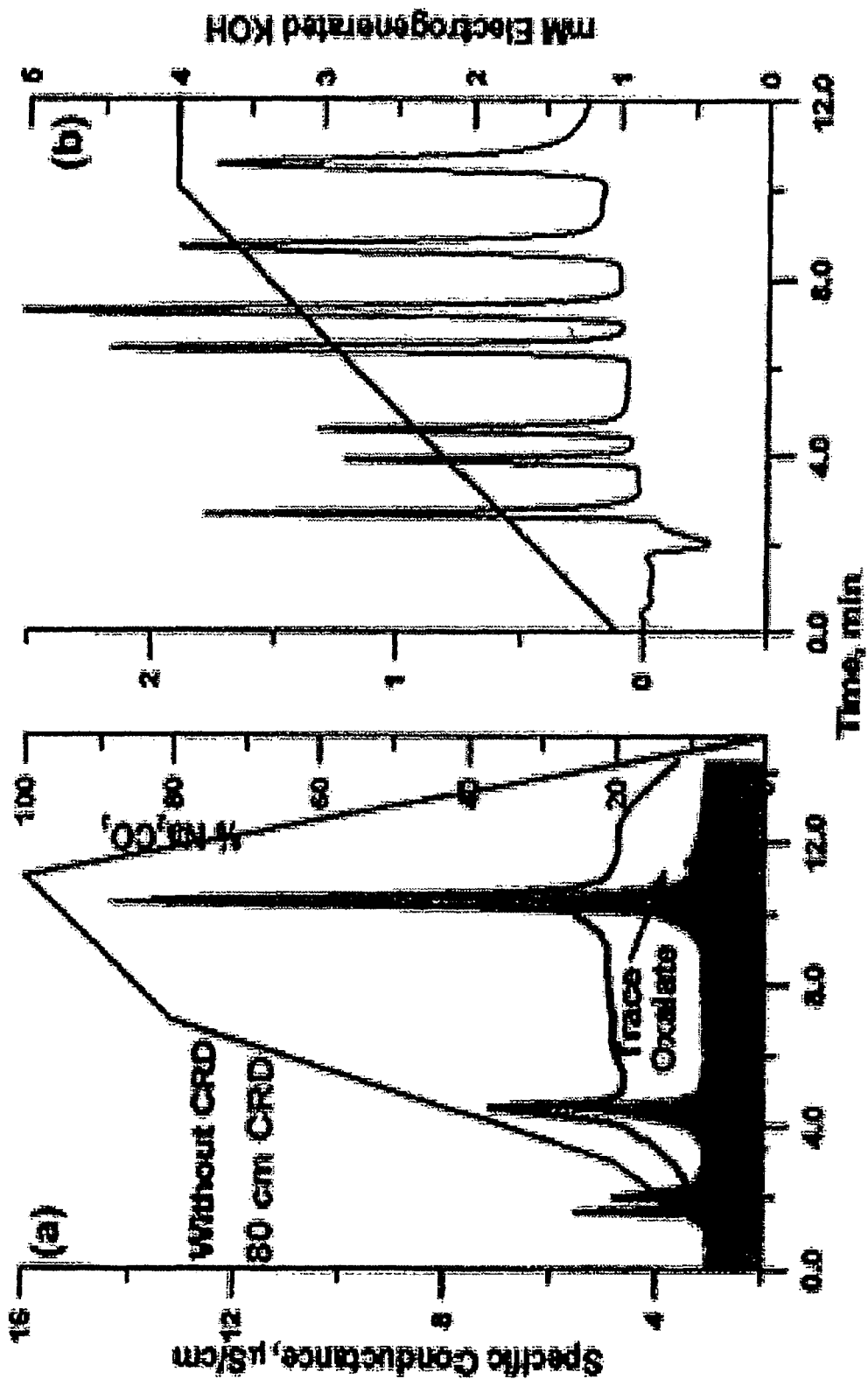
FIG. 10 shows carbonate gradient chromatograms (a) 4×100 mm AS11HC, 1 mL/min, gradient program 2.5 mM $NaHCO_3$ to 2.5 mM $Na_2CO_3$ as shown. 35 µL $Cl^-$ (1.5), $NO_2^-$ (2.1), $NO_3^-$ (7.7) and $SO_4^{2-}$ (31) injected, without (shaded solid) and with (dark line trace) a GRD at room temperature and (b) electrogenerated carbonate gradient (ref. 21), 2×50 mm AG12A+2×250 mm AS12A, 0.4 mL/min, 100 µL $F^-$ (1), $Cl^-$ (1), $NO_2^-$ (2), $Br^-$ (5), $NO_3^-$, (5), $SO_4^{2-}$, (10), $PO_4^{3-}$ (10). Eluent: 4 mM $NaHCO_3$ feed into electrodialytic generator with 1-4 mM KOH gradient over 10 min; concentrations in mg/L).

Ammonium carbonate gradients have been commonly used in liquid chromatography mass spectrometry due to the volatile nature of the buffer material. As already noted, the basic attractions of carbonate gradients has been previously discussed in the literature. It becomes particularly valuable with an efficiently functioning GRD. FIG. 10A shows such a chromatogram generated by running a gradient between 2.5 mM $NaHCO_3$ and 2.5 mM $Na_2CO_3$. At first sight, it may seem that this should not result in a change in the $H_2CO_3$ concentration reaching the detector but in fact the column sites are initially filled with bicarbonate and as divalent carbonate replaces the bicarbonate, one carbonate taking the place of two bicarbonate ions, the excess bicarbonate must come out of the column. The great difference with and without a GRD is readily apparent. FIG. 10B shows an electrodialytically generated gradient chromatogram according to Novic et al, *J. Chromatogr. A* 2002, 957, 165-172 demonstrating rapid separation of all seven common test ions.

Loss of other Weak Acid Analytes

The loss of other weak acid analytes through the GRD may be undesirable. However, the most obvious analytes susceptible to such loss, e.g., sulfide and cyanide are not sensitively detected in any case by suppressed conductometry. It is difficult to estimate exact loss of carboxylic acids such as formic and acetic acids in a comparison between heated and unheated systems because available thermodynamic data indicate that the dissociation constant of these carboxylic acids decreases with increasing temperature. In "area loss" experiments with and without the GRD under the presently recommended conditions of an oven enclosure at 30° C. no loss was discernible for these analytes.

If the GRD is designed with an external jacket that is concentric to the gas removal membrane, then the external fluid can also be operated in a low dispersion configuration. With such a geometry, gases that do transfer efficiently through the membrane, e.g., $H_2S$, HCN etc., can be detected in a second stream, selectively and sensitively with electrochemical detectors. We have used a similar arrangement to measure ammonia from an alkaline donor stream using a conductivity detector (data not shown).

In this work, we have demonstrated that efficient GRD units are easily constructed from inexpensively available membranes, are readily used with existing suppressor and detector systems and are of great benefit to atmospheric analysis and a variety of other applications.

Example 2

Figure 11:
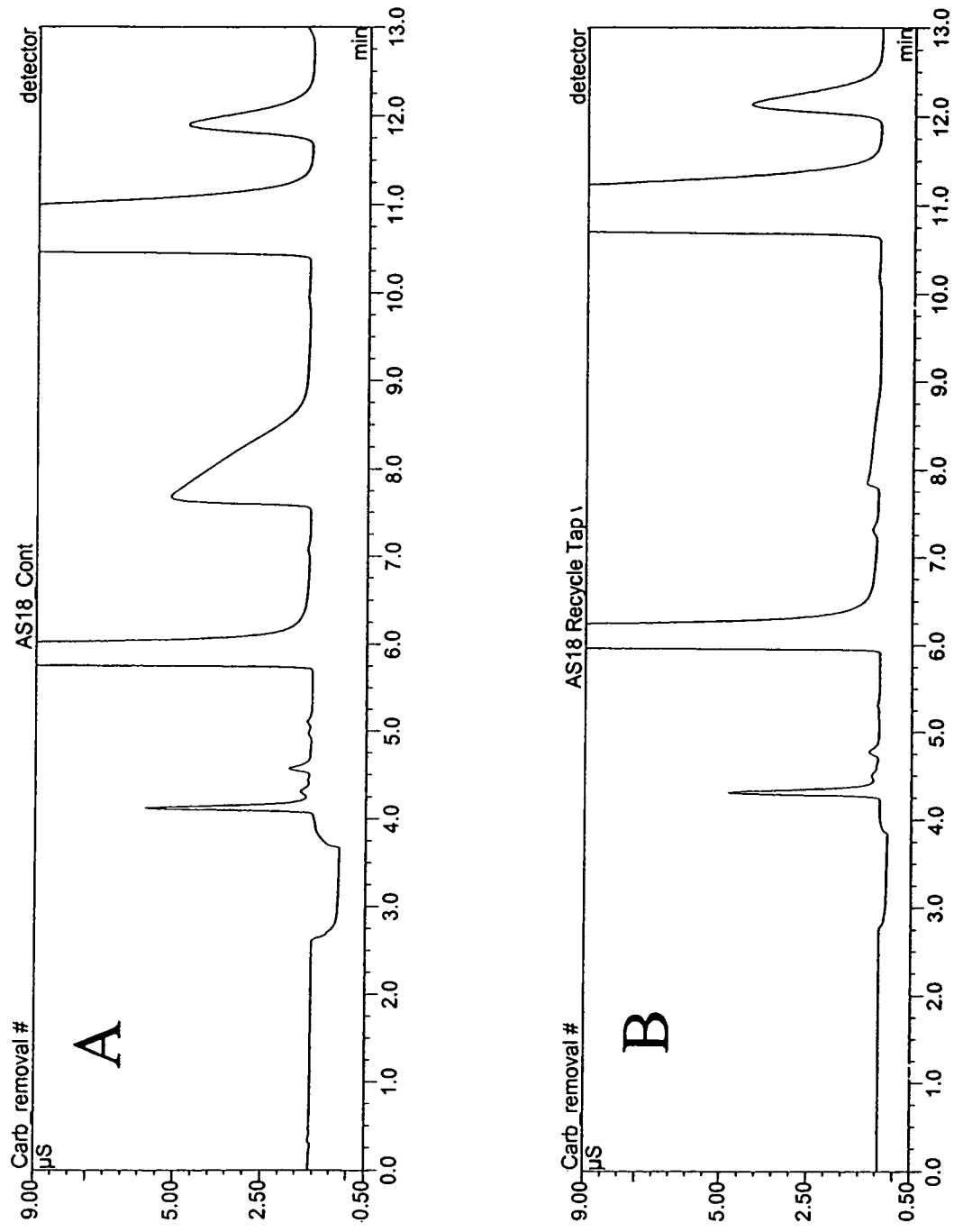
FIGS. 11A and B shows comparison chromatograms of a tap water sample obtained without and with a GRD installed using AS18 chemistry.

A DX600 system from Dionex Corp. was used in this work. A gas permeable tubing (400 um id.×150 cm length) as described in U.S. Pat. No. 5,439,736 was obtained from Neomecs (Eden Prairie, Minn.) and installed in a device as illustrated in FIG. 1. The device is designated as a GRD and is used for removal of carbon dioxide. The device was then installed as a post suppressor device as shown in FIG. 1. A large loop injection (1 mL sample loop) was done using a tap water sample. A control run was done without the GRD using AS18 chemistry and 23 mM NaOH at 1 ml/min (shown in FIG. 11A) and compared to a run done with the GRD (shown in FIG. 11B). The suppressor waste (a base) was diverted into the GRD as a fluidic flow to aid removal of the carbon dioxide and then diverted to waste. The results indicate a substantial portion of the carbonate peak is removed as per the present invention.

Example 3

Figure 12:
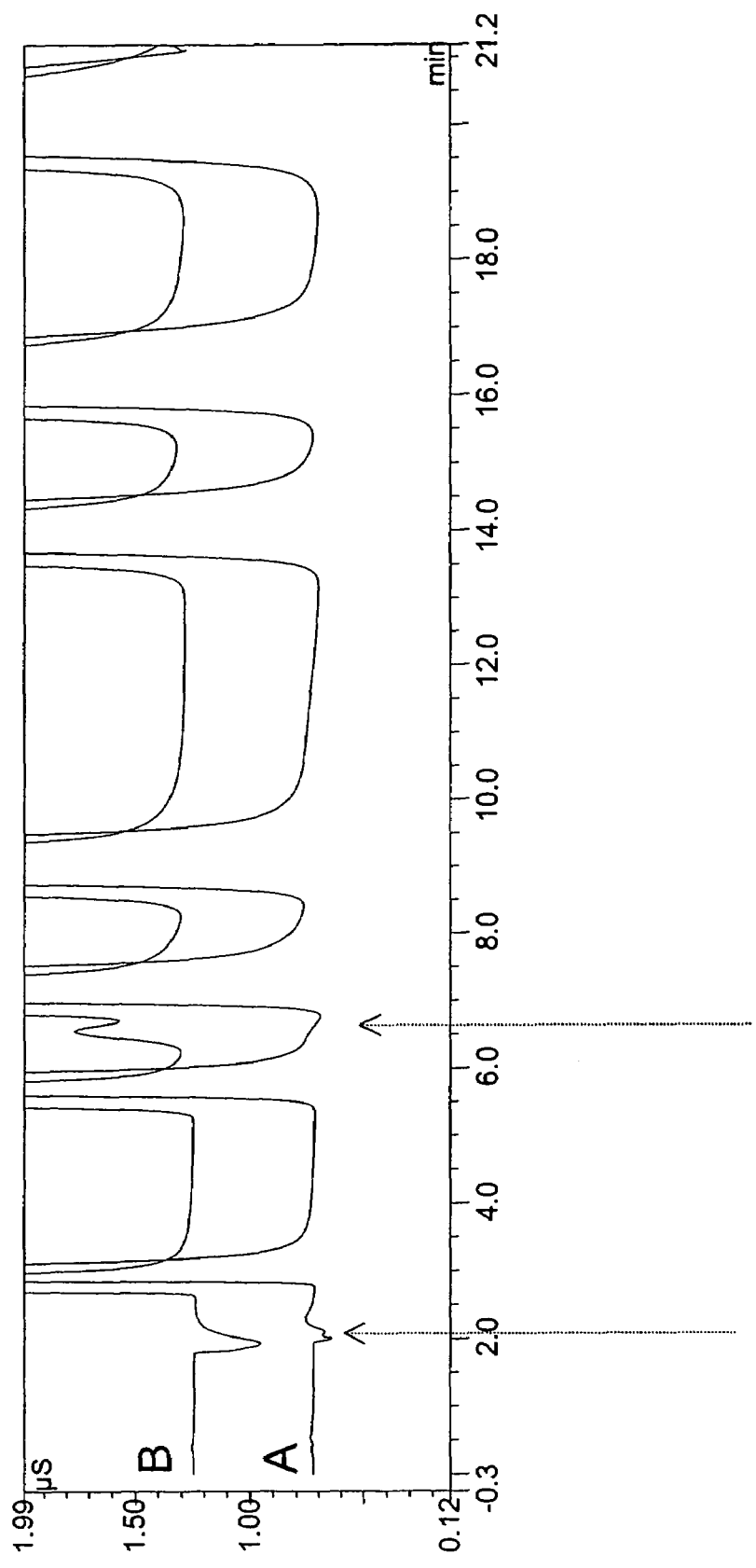
FIGS. 12A and B shows comparison chromatograms of a seven anion standard sample obtained without and with a GRD installed using proprietary column chemistry from Dionex Corp.

The experimental conditions were similar to Example 2 except a standard mixture comprising of 7 anion standards was analyzed with a proprietary column from Dionex Corp. with 38 mM NaOH at 1.2 mL/min flow rate and a 25 µL injection loop. The run done without the GRD (FIG. 12A) shows that the carbonate peak elutes close to Nitrite which makes it difficult to quantitate the Nitrite peak. The run done with the GRD (FIG. 12B) on the other hand showed removal of the peak corresponding to carbonate, thus leading to improved integration for Nitrite.

Example 4

Various lengths of the gas permeable tubing (209 um id.) as described in U.S. Pat. No. 5,439,736 were obtained from Neomecs. The tubings were assembled in devices similar to FIG. 1 and evaluated with a Dionex Corp. AS15 column with an eluent comprising of 38 mM NaOH at 0.3 mL/min at 30 C. The sample comprised of seven anion standards. The injection loop was 2.5 µL. The following table showed the effect of the GRD on the efficiency of the peaks. The early eluting chloride peak showed a bigger loss in efficiency than the later eluting sulfate peak. The presence of the GRD had very little impact on the later eluting sulfate peak. The optimal device length would be a compromise between $CO_2$ removal efficiency and peak efficiency.

| Length | Efficiency (chloride) | Efficiency (Sulfate) |
| --- | --- | --- |
| No GRD | 12899 | 11922 |
| 50 cm | 11521 | 11913 |
| 75 cm | 11141 | 11906 |
| 100 cm | 11303 | 11170 |
| 150 cm | 11014 | 11712 |

Example 5

Figure 13:
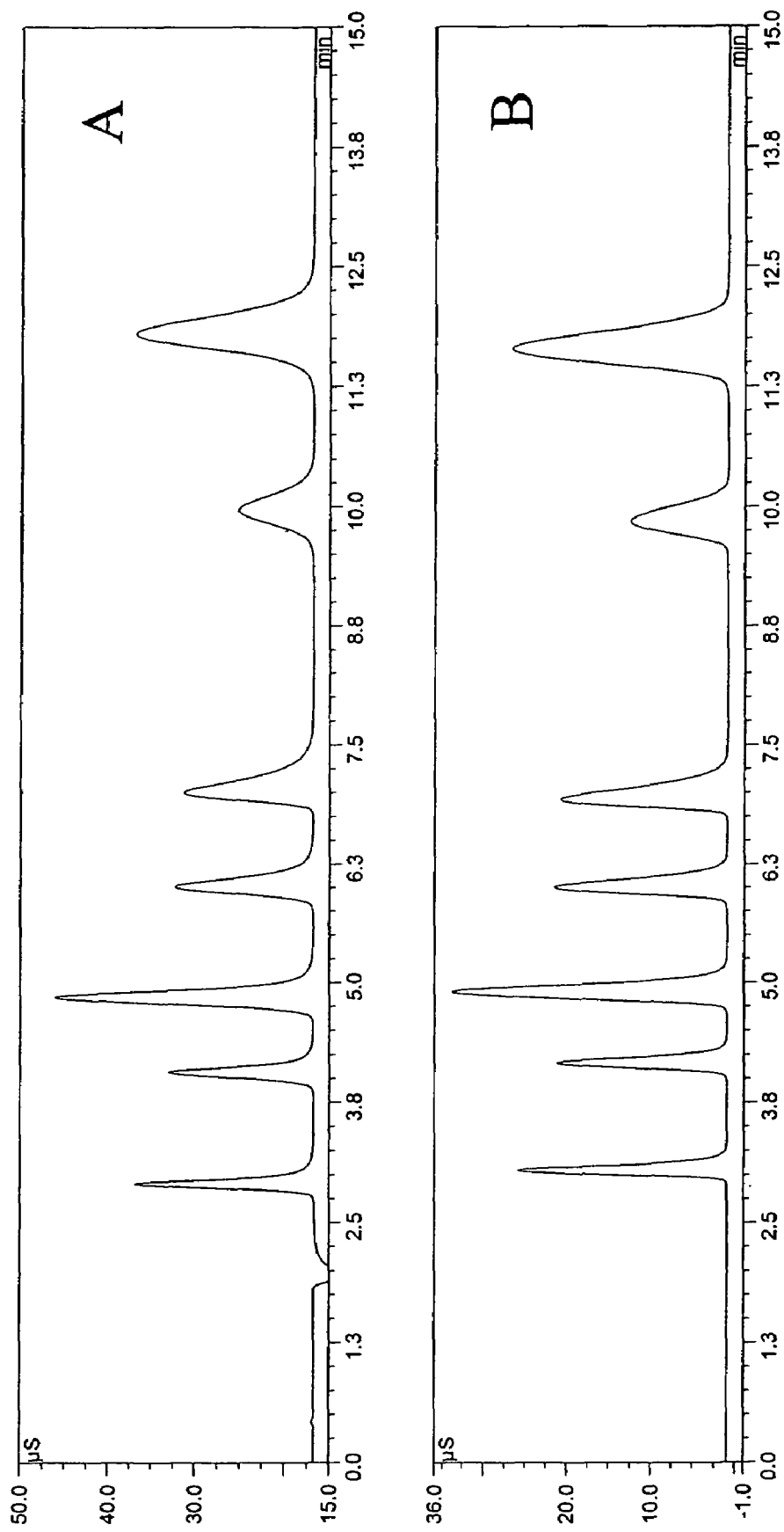
FIGS. 13A and B illustrates carbon dioxide removal from a suppressed carbonate eluent stream using AS14 chemistry.

A 120 cm tubing was coated following the procedure outlined in Example 2 and assembled into a device of FIG. 1. This unit was used as a post suppressor device to remove $CO_2$ from the suppressed eluent. An AS14 column from Dionex Corp. was used with 3.5 mM $NaHCO_3$ and 1 mM $Na_2CO_3$ eluent at a flow rate of 1.2 mL/min. A 25 mM NaOH solution was used as the external fluid and was dispensed into the GRD by using gravity feed. A 10× dilution of a seven anion standard from Dionex was used as the sample. FIG. 13B (GRD installed) showed a lower background of about 1 μS/cm versus about 16 μS/cm for the run done without the GRD installed (FIG. 13A). The peak response was also higher for all ions for the runs done with the GRD installed. The void peak was diminished with the GRD installed. All of the reported benefits of the GRD for bi carbonate and/or carbonate eluents by prior art devices were observed by the device of the present invention.

Example 6

A DX600 system from Dionex was used in this work. A gas permeable tubing (400 μm id.×150 cm length) as described in U.S. Pat. No. 5,439,736 was obtained from Neomecs (Eden Prairie, Minn.) and installed in a device of FIG. 1. The device was then installed to the injection valve as shown in FIG. 2 and without a suppressor device. A sample stream comprising of house DI water was pumped into the device using a pressurized reservoir. The outside of the gas permeable tubing was swept with 100 mM NaOH solution. The injection loop size was 1000 μL. The standard suppressed conductivity IC set up was used with an AS18 column and ASRS Ultra II suppressor. The eluent used was 23 mM KOH generated by a EG40 module at 1 mL/min. The sample stream was flowed into the injection loop in the load position and injected into the AS18 column. When the results were compared by bypassing the gas permeable tubing greater than 90% of the peak corresponding to carbonate was removed by the device of the present invention. The efficiencies of all the peaks when compared with and without the device of the present invention remain unchanged.

Example 7

The device of Example 6 was used with an AS15 column. The eluent used was 38 mM NaOH (bottled eluent). All other conditions were similar to Example 6 except a 100 μL injection of a seven anion standard mixture was done and the suppressor waste from the ASRS Ultra II suppressor was diverted into the encasing to sweep the outside of the permeable tubing. When the results were compared by bypassing the gas permeable tubing we observed greater than 90% of the peak corresponding to carbonate peak was removed by the device of the present invention. The efficiencies of all the peaks with and without the device of the present invention were unchanged. The peak corresponding to Nitrite could be integrated better without the carbonate interference with the device of the present invention.

Example 8

The experimental conditions were similar to Example 7 except a 1 mM NaOH sample spiked with seven anion standards and 100 ppm carbonate was used as the sample. The sample stream was suppressed using an ASRS Ultra suppressor prior to loading the sample onto the device of the present invention. The ASRS Ultra suppressor was operated in the external water mode in this experiment. The results indicated greater than 90% of the peak corresponding to carbonate was removed. The peak corresponding to Nitrite could be integrated better without the carbonate interference with the device of the present invention.

What is claimed is:

1. A liquid chromatographic system comprising:
   (a) a liquid chromatographic column having an inlet and an outlet,
   (b) a suppressor comprising a sample stream flow channel having an inlet and an outlet and separated by a permselective membrane from a regenerant stream flow channel having an inlet and an outlet, said liquid chromatographic column outlet in fluidic communication with the inlet of the said suppressor sample stream flow channel
   (c) a volatile component-removal device comprising a membrane comprising at least one porous wall, said device defining a liquid sample stream flow channel, having an inlet and an outlet, on one side of said membrane, and a receiving channel on the other side of said porous wall, said volatile component liquid sample stream flow channel inlet being in fluid communication with said suppressor sample stream outlet, and
   (d) said suppressor regenerant stream flow channel outlet being in fluid communication with said receiving channel of the volatile component-removal device.

2. The system of claim 1 in which said porous wall has a surface coated with a polymer permeable to said volatile component, said coating thickness being less than 10 μm.

3. The system of claim 1 further comprising:
   (c) a detector in fluid communication with said liquid sample stream flow channel outlet of said volatile component-removal device.

4. The system of claim 1 in which said volatile component-removal device membrane comprises tubing.

* * * * *